(12) United States Patent
Katoh et al.

(10) Patent No.: US 7,341,828 B2
(45) Date of Patent: Mar. 11, 2008

(54) THIOL COMPOUND, PHOTOPOLYMERIZATION INITIATOR COMPOSITION AND PHOTOSENSITIVE COMPOSITION

(75) Inventors: Tsuyoshi Katoh, Kanagawa (JP); Hirotoshi Kamata, Kanagawa (JP); Mina Onishi, Kanagawa (JP)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 10/505,778

(22) PCT Filed: Feb. 27, 2003

(86) PCT No.: PCT/JP03/02219

§ 371 (c)(1),
(2), (4) Date: Aug. 26, 2004

(87) PCT Pub. No.: WO03/072614

PCT Pub. Date: Sep. 4, 2003

(65) Prior Publication Data

US 2005/0153231 A1  Jul. 14, 2005

Related U.S. Application Data

(60) Provisional application No. 60/408,268, filed on Sep. 6, 2002.

(30) Foreign Application Priority Data

Feb. 28, 2002  (JP)  ............... 2002-052515
Sep. 3, 2002  (JP)  ............... 2002-257766

(51) Int. Cl.
*G03C 1/73* (2006.01)
*G03F 7/031* (2006.01)
*C08F 2/46* (2006.01)
*C07C 321/04* (2006.01)

(52) U.S. Cl. ............ 430/921; 430/916; 430/926; 430/270.1; 430/281.1; 430/286.1; 430/287.1; 522/27; 560/147

(58) Field of Classification Search ............... 430/921, 430/270.1, 926, 281.1, 286.1, 287.1; 560/147
See application file for complete search history.

(56) References Cited

U.S. PATENT DOCUMENTS

| | | | |
|---|---|---|---|
| 3,115,509 A * | 12/1963 | Mack ............. | 556/93 |
| 3,144,422 A * | 8/1964 | Homberg ............. | 524/302 |
| 4,020,233 A * | 4/1977 | Morgan ............. | 428/419 |
| 5,876,805 A | 3/1999 | Ostlie | |
| 6,455,207 B1 | 9/2002 | Katoh et al. | |
| 6,503,961 B1 * | 1/2003 | Okazaki et al. ............. | 522/173 |
| 2002/0115819 A1 * | 8/2002 | Primel et al. ............. | 528/373 |

FOREIGN PATENT DOCUMENTS

| | | |
|---|---|---|
| DE | 1 118 776 B | 12/1961 |
| EP | 0 900 800 A | 3/1999 |
| EP | 1 173 524 A1 | 1/2002 |
| JP | 10-253815 A | 9/1998 |
| WO | WO 01 25302 A | 4/2001 |

OTHER PUBLICATIONS

Scigalski et al (Chem. Abstract 2001:718595 for "Xanthene Dyes and Amino Acid Containing Thioether or Mercaptan Groups as Potential Components of Photoinitiating Compositions for Radical Polymerization", Polimery (2001), vol. 46(9), p. 613-621).*
Communication from Chinese Patent Office dated Jan. 10, 2006.
Chinese Office Action dated Mar. 23, 2007.

* cited by examiner

*Primary Examiner*—Sin J. Lee
(74) *Attorney, Agent, or Firm*—Sughrue Mion, PLLC

(57) ABSTRACT

A photopolymerization initiator composition containing a thiol compound having a mercapto group-containing group that has at least one substituent on the carbon atoms on carbon atom(s) at the $\alpha$- and/or $\beta$-position with respect to the mercapto group and a photopolymerization initiator; a photosensitive composition containing the composition; and a novel thiol compound for use in these compositions. The photosensitive composition containing the photopolymerizazion initiator composition of the present invention has high sensitivity and excellent storage stability and enables reduction in cost due by increasing productivity.

24 Claims, 12 Drawing Sheets

THIOL COMPOUND, PHOTOPOLYMERIZATION INITIATOR COMPOSITION AND PHOTOSENSITIVE COMPOSITION

CROSS-REFERENCE TO RELATED APPLICATION

This is an application based on the prescription of 35 U.S.C. Section 111 (a) with claiming the benefit of filing date of U.S. Provisional application Ser. No. 60/408,268 filed Sep. 6, 2002 under the provision of 35 U.S.C.111 (b), pursuant to 35 U.S.C. Section 119 (e) (1).

TECHNICAL FIELD

The present invention relates to a novel thiol compound, to a photopolymerization initiator composition containing the thiol compound having high sensitivity and excellent storage stability, and to a photosensitive composition containing the photopolymerization initiator composition.

BACKGROUND ART

Thiol compounds such as trimethylolpropane tris(3-mercaptopropionate) and pentaerythritol tetrakis(3-mercaptopropionate) are used widely in various applications in every kind of industrial field. Among them, the most general one is use of them for photosensitive compositions.

Photosensitive compositions are used in various fields including many fields such as printing plates, color proofs, color filters, solder resists, and photocuring ink. In particular, in recent years, room temperature, fast-curing and solventlessness, which are the most characteristic properties of photocuring, have received attention in various fields including these applications from the viewpoints of environmental pollution, energy saving, safety in working, production costs and the like and many studies and developments have been made on photosensitive compositions. In the development of color filters, studies on pigment dispersion type resist for color filters have been under way for the purpose of increasing productivity and achieving high precision. Also, in color proofs and printing plates, development has been under way for the purpose of achieving high speed and high precision in plate making. Further, solder resists for printed boards have been studied.

In these applications, there has been an increasing demand for photosensitive compositions and those which cure at lower energy, those which cure at higher rates, those which can form more precise patterns, those which have deeper curing depth, and those which have higher storage stability performance have been sought. Photosensitive compositions are mainly composed of a photopolymerization initiator composition, a compound having an ethylenically unsaturated bond which cures by a polymerization reaction and various kinds of additives, and the kinds of the components depend on use to which the photosensitive composition is applied.

Note that in the present invention, by the "photopolymerization initiator composition" is meant a composition containing at least one compound which participates in the initiation reaction of photopolymerization, such as a compound that generates a radical, an anion, or a cation by light, a compound having a chain transfer action, or a compound having sensitization activity.

The compounds which constitute the photopolymerization initiator composition are selected by their photosensitive wavelengths and polymerization initiating properties. The compound having an ethylenically unsaturated bond and the additives are selected by polymerizability and physical properties of a desired cured product. They are combined and used as a photosensitive composition. However, some compounds having an ethylenically unsaturated bond and some additives occasionally cause problems as follows in the photosensitive compositions. (1) Sufficient energy for initiating photopolymerization is not obtained; (2) storage stability is not obtained; (3) since irradiation light does not reach deep enough in a desired cured product due to the thickness thereof, curing proceeds only insufficiently; and (4) oxygen inhibition occurs at the portion where the photosensitive composition contacts the air. For these problems, various measures have been taken; for example, irradiation of greater light energy, use of an excess amount of a photopolymerization initiator and provision of an oxygen shielding membrane. Also for energy saving and reduction in production cost, a photosensitive composition having more excellent photocurability and storage stability is desired.

As for the photopolymerization initiator composition containing a thiol compound, Japanese Patent Application Laid-open No. Hei 10-253815 discloses a photopolymerizable composition containing a polyfunctional thiol and an initiator selected from a group consisting of a biimidazole compound, a titanocene compound, a triazine compound and an oxazole compound. Japanese Patent Application Laid-open No. 2000-249822 (EP1031579A2, U.S. Pat. No. 6,455,207) discloses a photopolymerization initiator containing a sensitizer, an organic boron complex and a compound having a mercapto group. However, the attempt of achieving high sensitivity by use of such a polyfunctional thiol compound causes a problem of costing the storage stability.

The inventors of the present invention have found that in order to obtain a photosensitive composition which has high sensitivity and excellent photocurability as well as excellent storage stability, selection of a photopolymerization initiator composition is important; in particular, selection of a thiol compound used as one component of the photopolymerization initiator composition is important.

Therefore, an object of the present invention is to provide a photopolymerization initiator composition having high sensitivity and excellent storage stability, a photosensitive composition containing the photopolymerization initiator composition, and a novel thiol compound suitable for the photopolymerization initiator composition.

SUMMARY OF THE INVENTION

The inventors of the present invention have found that the above-mentioned problems are solved by using a thiol compound having a structure in which carbon atom(s) at the α- and/or β-position with respect to the mercapto group have a substituent as one component of the photopolymerization initiator composition to be contained in a photosensitive composition, thereby achieving the present invention.

The polyfunctional thiols disclosed or used in the above-mentioned publications are all those whose carbon chain bonded to the mercapto group is a straight chain but those whose carbon chain have a branched structure as referred to in the present invention are not disclosed.

The present invention relates to the following photopolymerization initiator compositions, to the following novel thiol compounds suitable for the composition, and to the following photosensitive compositions.

1. A photopolymerization initiator composition, comprising a thiol compound having a mercapto group-containing group that has at least one substituent on carbon atom(s) at the α- and/or β-position to the mercapto group and a photopolymerization initiator.
2. The photopolymerization initiator composition as described in 1 above, wherein at least one of the substituent on carbon atoms at the α- and/or β-position to the mercapto group is an alkyl group.
3. The photopolymerization initiator composition as described in 2 above, wherein the alkyl group is a straight chain or branched chain alkyl group having 1 to 10 carbon atoms.
4. The photopolymerization initiator composition as described in 1 above, wherein the thiol compound is a compound having two or more mercapto group-containing groups.
5. The photopolymerization initiator composition as described in 1 or 4 above, wherein the thiol compound is a compound comprising a mercapto group-containing group represented by formula (1)

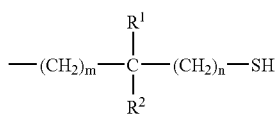
(1)

wherein $R^1$ and $R^2$ represent each independently a hydrogen atom or an alkyl group having 1 to 10 carbon atoms, provided that at least one of $R^1$ and $R^2$ is an alkyl group, m is 0 or an integer of 1 to 2, and n is 0 or 1.

6. The photopolymerization initiator composition as described in 5 above, wherein the thiol compound having a mercapto group-containing group is an ester compound derived from a mercapto group-containing carboxylic acid represented by formula (2) and a polyfunctional alcohol

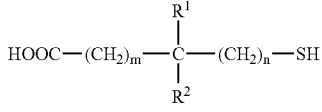
(2)

wherein the symbols have the same meaning as defined in 5 above.

7. The photopolymerization initiator composition as described in 6 above, wherein the polyfunctional alcohol is one or more compounds selected from a group consisting of an alkylene glycol (provided that the alkylene group has 2 to 10 carbon atoms and may be branched), diethylene glycol, dipropylene glycol, glycerol, trimethylolpropane, pentaerythritol, and dipentaerythritol.
8. The photopolymerization initiator composition as described in 7 above, wherein the alkylene glycol is ethylene glycol, 1,2-propylene glycol or 1,2-butanediol.
9. The photopolymerization initiator composition as described in 6 above, wherein the thiol compound is a compound represented by formula (A)

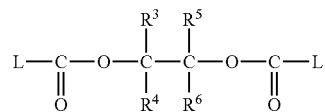
(A)

wherein $R^3$ to $R^6$ represent each independently a hydrogen atom or an alkyl group having 1 to 10 carbon atoms, and L is a group represented by formula (1)

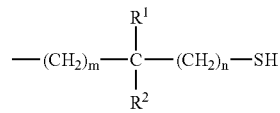
(1)

wherein $R^1$, $R^2$, m and n have the same meanings as defined in 5 above.

10. The photopolymerization initiator composition as described in 6 above, wherein the thiol compound is a compound represented by formula (B)

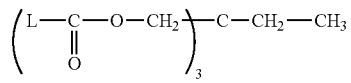
(B)

wherein L is a group represented by formula (1)

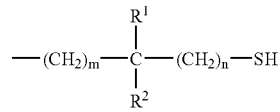
(1)

wherein $R^1$, $R^2$, m and n have the same meanings as defined in 5 above.

11. The photopolymerization initiator composition as described in 5, 6, 9 or 10 above, wherein n is 0.
12. The photopolymerization initiator composition as described in 5, 6, 9 or 10 above, wherein m is 0 or 1.
13. The photopolymerization initiator composition as described in 6 above, wherein the thiol compound having a mercapto group-containing group is a compound selected from ethylene glycol bis(3-mercaptobutyrate), 1,2-propylene glycol (3-mercaptobutyrate), trimethylolpropane tris(3-mercaptobutyrate), ethylene glycol bis(2-mercaptoisobutyrate), 1,2-propylene glycol bis(2-mercaptoisobutyrate), and trimethylolpropane tris(2-mercaptoisobutyrate).
14. The photopolymerization initiator composition as described in 1 above, wherein the photopolymerization initiator is at least one photopolymerization initiator selected from a group consisting of α-hydroxyacetophenones, α-aminoacetophenones, and biimidazoles.
15. The photopolymerization initiator composition as described in 1 above, wherein the composition further comprises a sensitizer.

16. The photopolymerization initiator composition as described in 15 above, wherein the sensitizer is selected from a group consisting of benzophenones and anthraquinones.
17. A photosensitive composition containing the photopolymerization initiator composition as described in any one of 1 to 16 above.
18. The photosensitive composition as described in 17 above, wherein the composition contains a polymer compound and/or a compound having an ethylenically unsaturated bond.
19. The photosensitive composition as described in 18 above, wherein the polymer compound is soluble in a solvent or an aqueous alkali solution.
20. The photosensitive composition as described in 17 above, wherein the composition contains a pigment.
21. A thiol compound which is an ester compound derived from a mercapto group-containing carboxylic acid represented by formula (2) and a polyfunctional alcohol

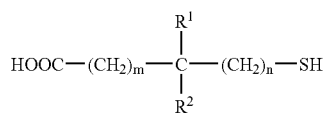

wherein $R^1$ and $R^2$ represent each independently a hydrogen atom or an alkyl group having 1 to 10 carbon atoms, provided that at least one of $R^1$ and $R^2$ is an alkyl group, m is 0 or an integer of 1 to 2, and n is 0 or 1.
22. The thiol compound as described in 21 above, wherein the polyfunctional alcohol is one or more compounds selected from a group consisting of an alkylene glycol (provided that the alkylene group has 2 to 10 carbon atoms and may be branched), diethylene glycol, dipropylene glycol, glycerol, trimethylolpropane, pentaerythritol, and dipentaerythritol.
23. The thiol compound as described in 22 above, wherein the alkylene glycol is ethylene glycol, 1,2-propylene glycol or 1,2-butanediol.
24. The thiol compound as described in 21 above, wherein the thiol compound is represented by formula (A)

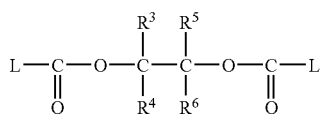

wherein $R^3$ to $R^6$ represent each independently a hydrogen atom or an alkyl group having 1 to 10 carbon atoms, and L is a group represented by formula (1)

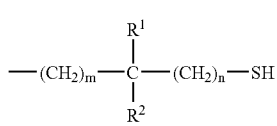

wherein $R^1$, $R^2$, m and n have the same meanings as defined in 21 above.
25. The thiol compound as described in 21 above, wherein the thiol compound is represented by formula (B)

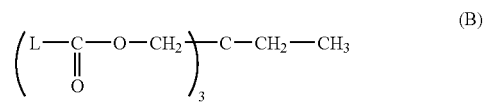

wherein L is a group represented by formula (1)

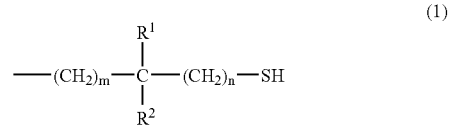

wherein $R^1$, $R^2$, m and n have the same meanings as defined in 21 above.
26. The thiol compound as described in 21, 24 or 25 above, wherein n is 0.
27. The thiol compound as described in 21, 24 or 25 above, wherein m is 0 or 1.
28. The thiol compound as described in 21 above, wherein the thiol compound has a molecular weight of 200 to 1,000.
29. The thiol compound as in 21 above, wherein the thiol compound having a mercapto group-containing group is a compound selected from ethylene glycol bis(3-mercapto-butyrate), 1,2-propylene glycol (3-mercapto-butyrate), trimethylolpropane tris(3-mercaptobutyrate), ethylene glycol bis(2-mercaptoisobutyrate), 1,2-propylene glycol bis(2-mercaptoisobutyrate), and trimethylolpropane tris (2-mercaptoisobutyrate).

DETAILED DESCRIPTION

Figure 1:
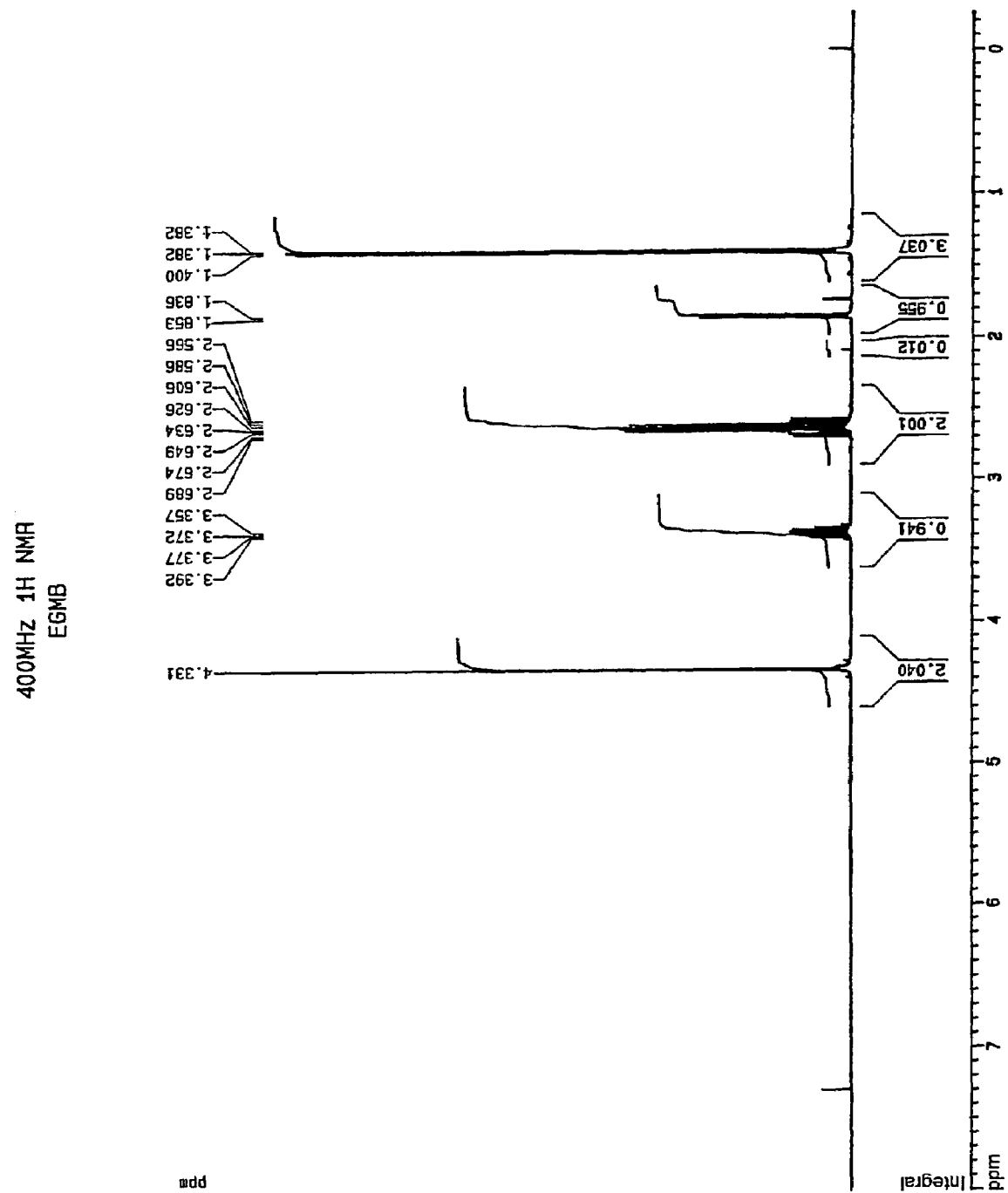
FIG. 1 and FIG. 2 are diagrams showing a $^1$H-NMR spectrum and $^{13}$C-NMR spectrum of ethylene glycol bis(3-mercaptobutyrate) (EGMB)

1. Thiol Compound (1) Thiol Compound Having a Mercapto Group-Containing Group

The thiol compound of the present invention is a thiol compound having a specific mercapto group-containing group, characterized in that the mercapto group-containing group is of a structure having at least one substituent on carbon atom(s) at the α- and/or β-position with respect to the mercapto group. It is preferred that at least one of the substituents be an alkyl group.

The structure in which carbon atom(s) at the α- and/or β-position with respect to the mercapto group have a substituent means a structure having a branching at the carbon atoms at the α- and/or β-position with respect to the mercapto group, in other words, a so-called branched structure in which the carbon atoms at the α- and/or β-position with respect to the mercapto group each combine with three or more atoms other than hydrogens. The case where at least one of the substituents is an alkyl group means that at least one of substituents at the α- and/or β-position with respect to the mercapto group other than main chain is an alkyl group. Here, the main chain indicates the longest structure containing a mercapto group constituted by atoms other than hydrogens.

As the mercapto group-containing group, a group represented by the following formula (1) is preferred.

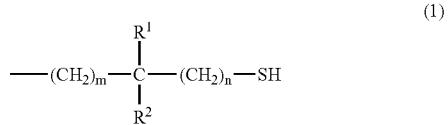

(1)

In the formula (1) above, $R^1$ and $R^2$ represent each independently a hydrogen atom or an alkyl group having 1 to 10 carbon atoms, provided that at least one of $R^1$ and $R^2$ is an alkyl group. That is, both of $R^1$ and $R^2$ are not hydrogen atoms simultaneously. In the case where $R^1$ and $R^2$ are both alkyl groups, they may be the same or different.

The alkyl groups having 1 to 10 carbon atoms represented by $R^1$ and $R^2$ may be of a straight chain or branched chain. Examples thereof include, a methyl group, an ethyl group, an n-propyl group, an iso-propyl group, an n-butyl group, an iso-butyl group, a tert-butyl group, an n-hexyl group, and an n-octyl group, preferably a methyl group and an ethyl group.

With respect to the symbols m and n, m is 0 or an integer of 1 to 2, preferably 0 or 1, and n is 0 or 1, preferably 0.

The thiol compound of the present invent in is preferably a polyfunctional thiol compound having two or more mercapto group-containing groups. Specifically, a polyfunctional thiol compound having two or more of the above-mentioned mercapto group-containing groups is more preferred.

Thus, by being polyfunctional, the thiol compound enables photopolymerization with even higher sensitivity as compared with monofunctional compounds.

The thiol compound of the present invention is preferably one in which the mercapto group-containing group represented by the above-mentioned formula (1) assumes the structure of a carboxylic acid derivative as represented by the formula (3) below.

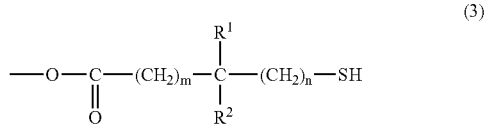

(3)

Such a thiol compound of the present invention is preferably an ester of a mercapto group-containing carboxylic acid represented by formula (2) below and an alcohol.

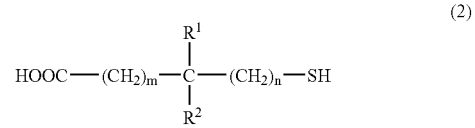

(2)

The alcohol is preferably a polyfunctional alcohol. Use of the polyfunctional alcohol can give rise to a polyfunctional thiol compound after an esterification reaction.

Examples of the polyfunctional alcohol include an alkylene glycol (provided that the alkylene group has 2 to 10 carbon atoms and may be branched), diethylene glycol, glycerol, dipropylene glycol, trimethylolpropane, pentaerythritol, and dipentaerythritol. Examples of the alkylene glycol include ethylene glycol trimethylene glycol, 1,2-propylene glycol, 1,2-butanediol, 1,3-butanediol, 2,3-butanediol, and tetramethylene glycol.

Preferred polyfunctional alcohols are alkylene glycols whose main chain has 2 carbon atoms, such as ethylene glycol, 1,2-propylene glycol, and 1,2-butanediol, and trimethylolpropane.

As the mercapto group-containing group of the formula (2) above, 2-mercaptopropionic acid, 3-mercaptobutyric acid, 2-mercaptoisobutyric acid, 3-mercaptoisobutyric acid, and the like may be exemplified.

Specific examples of the thiol compound of the present invention having the structure of the formula (1) above include the following compounds.

As hydrocarbon dithiols, 2,5-hexanedithiol, 2,9-decanedithiol, 1,4-bis(1-mercaptoethyl)benzene, and the like may be exemplified.

As compounds containing an ester bond structure, di(1-mercaptoethyl) phthalate, di(2-mercaptopropyl) phthalate, di(3-mercaptobutyl) phthalate, di(3-mercapto-isobutyl) phthalate, and the like may be exemplified.

Preferred examples thereof include
ethylene glycol bis(3-mercaptobutyrate),
propylene glycol bis(3-mercaptobutyrate),
diethylene glycol bis(3-mercaptobutyrate),
butanediol bis(3-mercaptobutyrate),
octanediol bis(3-mercaptobutyrate),
trimethylolpropane tris(3-mercaptobutyrate),
pentaerythritol tetrakis(3-mercaptobutyrate),
dipentaerythritol hexakis(3-mercaptobutyrate),
ethylene glycol bis(2-mercaptopropionate),
propylene glycol bis(2-mercaptopropionate),
diethylene glycol bis(2-mercaptopropionate),
butanediol bis(2-mercaptopropionate),
octanediol bis(2-mercaptopropionate),
trimethylolpropane tris(2-mercaptopropionate),
pentaerythritol tetrakis(2-mercaptopropionate),
dipentaerythritol hexakis(2-mercaptopropionate),
ethylene glycol bis(3-mercaptoisobutyrate),
propylene glycol bis(3-mercaptoisobutyrate),
diethylene glycol bis(3-mercaptoisobutyrate),
butanediol bis(3-mercaptoisobutyrate),
octanediol bis(3-mercaptoisobutyrate),
trimethylolpropane tris(3-mercaptoisobutyrate),
pentaerythritol tetrakis(3-mercaptoisobutyrate),
dipentaerythritol hexakis(3-mercaptoisobutyrate),
ethylene glycol bis(2-mercaptoisobutyrate),
propylene glycol bis(2-mercaptoisobutyrate),
diethylene glycol bis(2-mercaptoisobutyrate),
butanediol bis(2-mercaptoisobutyrate), octanediol bis(2-mercaptoisobutyrate),
trimethylolpropane tris(2-mercaptoisobutyrate),
pentaerythritol tetrakis(2-mercaptoisobutyrate),
dipentaerythritol hexakis(2-mercaptoisobutyrate),
ethylene glycol bis(4-mercaptovalerate),
propylene glycol bis(4-mercaptoisovalerate),
diethylene glycol bis(4-mercaptovalerate),
butanediol bis(4-mercaptovalerate),
octanediol bis(4-mercaptovalerate),
trimethylolpropane tris(4-mercaptovalerate),
pentaerythritol tetrakis(4-mercaptovalerate),
dipentaerythritol hexakis(4-mercaptovalerate),
ethylene glycol bis(3-mercaptovalerate),
propylene glycol bis(3-mercaptovalerate),
diethylene glycol bis(3-mercaptovalerate),
butanediol bis(3-mercaptovalerate),
octanediol bis(3-mercaptovalerate),
trimethylolpropane tris(3-mercaptovalerate),
pentaerythritol tetrakis(3-mercaptovalerate), and
dipentaerythritol hexakis(3-mercaptovalerate).

The molecular weight of the thiol compound of the present invention is not particularly limited but is preferably 200 to 1,000.

The production method for the thiol compound of the present invention is not particularly limited. As for the esters of a mercapto group-containing carboxylic acid and an alcohol can be obtained by reacting the mercapto group-containing carboxylic acid represented by the aforementioned formula (2) and an alcohol by a conventional method to form an ester. The conditions of the esterification reaction are not particularly limited and may be selected from a group consisting of the hitherto known reaction conditions appropriately.

(2) Thiol Compounds (A) and (B)

More preferred examples of thiol compounds include thiol compounds (A) and (B) described below.

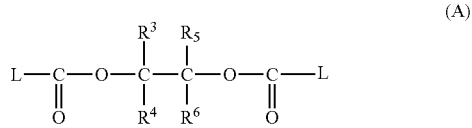

In formula (A), $R^3$ to $R^6$ represent each independently a hydrogen atom or an alkyl group having 1 to 10 carbon atoms. The alkyl group is preferably a straight chain or branched chain alkyl group having 1 to 3 carbon atoms. Specific examples thereof include a methyl group, an ethyl group, an n-propyl group, and an iso-propyl group, and more preferably a methyl group and an ethyl group. More preferably, $R^3$ is a hydrogen atom, a methyl group or an ethyl group, and $R^4$ to $R^6$ are hydrogen atoms. L is a mercapto group-containing group represented by the aforementioned formula (1).

The thiol compound (A) is a compound having two mercapto group-containing groups obtained by using a diol whose main chain has 2 carbon atoms as a starting material polyfunctional alcohol. More preferred examples of the thiol compound (A) include those in which the mercapto group is of a secondary group (A1) and those in which the mercapto group is of a tertiary group (A2).

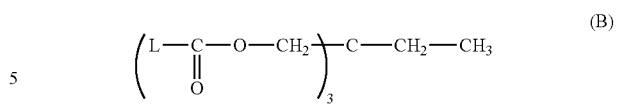

In formula (B), L is a mercapto group-containing group represented by the aforementioned formula (1). The thiol compound (B) is a compound having three mercapto group-containing groups obtained by using trimethylolpropane as a starting material polyfunctional alcohol. More preferred examples of the thiol compound (B) include those in which the mercapto group is of a secondary group (B3) and those in which the mercapto group is of a tertiary group (B4).

As described above, particularly preferred examples of the novel thiol compound of the present invention include four kinds of thiol compounds (A1), (A2), (B3) and (B4). Hereinafter, they are described in detail.

A1: Thiol compound in which the mercapto group is of a secondary group obtained using a diol having two carbon atoms as a starting material polyfunctional alcohol;

This thiol compound is a thiol compound represented by the formula (A) above, wherein either $R^1$ or $R^2$ in L (the mercapto group-containing group represented by the formula (1)) is a hydrogen atom, and n=0. Examples of the diol having 2 carbon atoms in the main chain include ethylene glycol, 1,2-propylene glycol, and 1,2-butanediol. Preferred specific examples of such a thiol compound (A1) include ethylene glycol bis(3-mercaptobutyrate), 1,2-propylene glycol bis(3-mercaptobutyrate), and 1,2-butanediol bis(3-mercaptobutyrate).

A2: Thiol compound in which the mercapto group is of a tertiary group obtained using a diol having two carbon atoms as a starting material polyfunctional alcohol;

This thiol compound is a thiol compound represented by the formula (A) above, wherein both of $R^1$ and $R^2$ in L (the mercapto group-containing group represented by the formula (1)) are alkyl groups, and n=0. Preferred specific examples of such a thiol compound (A2) include ethylene glycol bis(2-mercaptoisobutyrate) and 1,2-propylene glycol bis(2-mercaptoisobutyrate).

B3: Thiol compound in which the mercapto group is of a secondary group obtained using a trimethylolpropane as a starting material polyfunctional alcohol;

This thiol compound is a thiol compound represented by the formula (B) above, wherein either $R^1$ or $R^2$ in L (the mercapto group-containing group represented by the formula (1)) is a hydrogen atom, and n=0. Preferred specific examples of such a thiol compound (B3) include trimethylolpropane tris(3-mercaptobutyrate).

B4: Thiol compound in which the mercapto group is of a tertiary group obtained using a trimethylolpropane as a starting material polyfunctional alcohol;

This thiol compound is a thiol compound represented by the formula (B) above, wherein both of $R^1$ and $R^2$ in L (the mercapto group-containing group represented by the formula (1)) are alkyl groups, and n=0. Preferred specific examples of such a thiol compound (B4) include trimethylolpropane tris(2-mercaptoisobutyrate).

2. Photopolymerization Initiator Composition and Photosensitive Composition Containing the Same (1) Photopolymerization Initiator Composition The photopolymerization initiator composition of the present invention contains a thiol compound as described above and a photopolymerization initiator.

The thiol compound may be used singly or two or more of them may be used in combination.

As the photopolymerization initiator, general photopolymerization initiators may be used. Preferred examples thereof include α-hydroxyacetophenones, α-aminoacetophenones, and biimidazoles.

Examples of the α-hydroxyacetophenones include
2-hydroxy-2-methyl-1-phenylpropan-1-one,
2-hydroxy-2-methyl-1-phenylbutan-1-one,
1-(4-methylphenyl)-2-hydroxy-2-methylpropan-1-one,
1-(4-isopropylphehyl)-2-methylpropan-1-one,
1-(4-butylphehyl)-2-hydroxy-2-methylpropan-1-one,
2-hydroxy-2-methyl-1-(4-octylphenyl)propan-1-one,
1-(4-dodecylphehyl)-2-methylpropan-1-one,
1-(4-methoxyphehyl)-2-methylpropan-1-one,
1-(4-methylthiophehyl)-2-methylpropan-1-one,
1-(4-chlorophehyl)-2-hydroxy-2-methylpropan-1-one,
1-(4-bromophehyl)-2-hydroxy-2-methylpropan-1-one,
2-hydroxy-1-(4-hydroxyphenyl)-2-methylpropan-1-one,
1-(4-dimethylaminophehyl)-2-hydroxy-2-methylpropan-1-one,
1-(4-carboethoxyphehyl)-2-hydroxy-2-methylpropan-1-one,
1-hydroxycyclohexylphenyl ketone, and
2-hydroxy-1-(4-(2-hydroxyethoxy)phenyl)-2-methylpropan-1-one.

Examples of the α-aminoacetophenones include
2-dimethylamino-2-methyl-1-phenylpropan-1-one,
2-diethylamino-2-methyl-1-phenylpropan-1-one,
2-methyl-2-morpholino-1-phenylpropan-1-one,
2-dimethylamino-2-methyl-1-(4-methylphenyl)propan-1-one,
2-dimethylamino-1-(4-ethylphenyl)-2-methylpropan-1-one,
2-dimethylamino-1-(4-isopropylphenyl)-2-methylpropan-1-one,
1-(4-butylphenyl)-2-dimethylamino-2-methylpropan-1-one,
2-dimethylamino-1-(4-methoxyphenyl)-2-methylpropan-1-one,
2-dimethylamino-2-methyl-1-[4-(methylthio)phenyl]propan-1-one,
2-methyl-1-[4-(methylthio)phenyl]-2-morpholinopropan-1-one,
2-benzyl-2-dimethylamino-1-(4-morpholinophenyl)butan-1-one, and
2-benzyl-2-dimethylamino-1-(4-dimethylaminophenyl)butan-1-one.

Examples of the biimidazoles include
2,2'-bis(2-chlorophenyl)-4,4',5,5',-tetraphenyl-1,2'-biimidazol,
2,2'-bis(2-chlorophenyl)-4,4', 5,5"-tetra(ethoxyphenyl)-1,2'-biimidazole,
2,2'-bis(2-chlorophenyl)-4,4',5,5'-tetra(4-bromophenyl)-1,2'-biimidazole,
2,2'-bis(2-chlorophenyl)-4,4',5,5'-tetra(4-methylphenyl)-1,2'-biimidazole,
2,2'-bis(2-chlorophenyl)-4,4',5,5'-tetra(4-ethylphenyl)-1,2'-biimidazole,
2,2'-bis(2-chlorophenyl)-4,4',5,5'-tetra(4-butylphenyl)-1,2'-biimidazole,
2,2'-bis(2-chlorophenyl)-4,4',5,5'-tetra(4-octylphenyl)-1,2'-biimidazole,
2,2'-bis(2-chlorophenyl)-4,4',5,5'-tetra(4-methoxylphenyl)-1,2'-biimidazole,
2,2'-bis(2-chlorophenyl)-4,4',5,5',-tetra(3-methoxylphenyl)-1,2'-biimidazole,
2,2'-bis(2,4-dichlorophenyl)-4,4',5,5'-tetraphenyl-1,2'-biimidazole,
2,2'-bis(2-chlorophenyl)-4,4',5,5'-tetra(3-methoxylphenyl)-1,2'-biimidazole,
2,2'-bis(2,4-difluorophenyl)-4,4',5,5'-tetra(3-methoxy-phenyl)-1,2'-biimidazole, and
2,2'-bis(2-methylphenyl)-4,4',5,5'-tetraphenyl-1,2'-biimidazole.

As the photopolymerization initiator other than those described above, benzoin methyl ether, benzoin ethyl ether, benzoin isopropyl ether, benzyl methyl ketal, α-halogenoacetophenones, methyl phenyl glyoxylate, benzyl, anthraquinone, phenanthrenequinone, camphor quinone isophthalophenone, acylphosphine oxide and the like may be used.

These photopolymerization initiators may be used singly or two or more of them may be used in combination.

In the photopolymerization initiator composition, the content of the thiol compound is preferably 10 to 90% by mass, and the content of the photopolymerization initiator is preferably 90 to 10% by mass.

To further increase the sensitivity of the photopolymerization initiator composition, a sensitizer may be used.

Examples of the sensitizer include cation dyes such as cyanine, xanthene, oxazine, thiazine, diarylmethane, triarylmethane, and pyrilium, neutral dyes such as merocyanine, coumarin, indigo, aromatic amines, phthalocyanine, azo, quinone, and thioxanthene sensitizing dyes, and compounds such as benzophenones, acetophenones, benzoins, thioxanthones, anthraquinones, imidazoles, biimidazoles, coumarins, ketocoumarins, triphenylpyriliums, triazines, and benzoic acids. Also, acylphosphine oxide, methyl phenyl glyoxylate, α-acyl oxime ester, benzyl, camphor quinones and the like compounds may be used.

Here, the counter anions in the case of cation dyes may be any anion, examples of which include halogen ions such as chlorine ion, bromine ion, and iodide ion, benzenesulfonate anion, p-toluenesulphonate anion, methanesulfonate anion, $BF_4$ anion, $PF_6$ anion, and perchlorate anion.

These compounds may be used singly or two or more of them may be used in combination as the sensitizer. However, they must be determined in consideration of the light emission pattern of the light source used.

The cation dyes include cation dyes such as Crystal Violet (C. I. 42555), Methyl Violet (C. I. 42535), Malachite Green (C. I. 42000), Fuchsin (C. I. 42510), Crystal Violet-Carbinol Base (C. I. 42555:1), Parafuchsin (C. I. 42500), Rhodamine B (C. I. 45170), Victoria Blue B (C. I. 44045), Victoria Pure Blue BOH(C. I. 42595), Brilliant Green (C. I. 42040), Night Blue BX (C. I. 51185), Neutral Red (C. I. 50040), Basic Yellow 1, 11, 13, 21, 28, 36, and Basic Orange 21, 22, and Basic Red 1 (C. I. 45160), Basic Red 5 (C. I. 50040), Basic Red 13 (C.I. 48015), Basic Violet 7 (C. I. 48020), Basic Violet 11 (C. I. 45175), Crystal Violet p-toluenesulfonate, or naphthalene sulfonate, Victoria Blue B p-toluenesulfonate or perchlorate, Basic Orange 21 p-toluenesulfonate or $BF_4$ salt, and Basic Red 5 naphthalenesulfonate or $PF_6$ salt.

Electrically neutral dyes include
3-aryl-1-carboxymethyl-5-[2-(3-ethyl-2-(3H)-benzoxazolyl-idene)-2-thiohydantoin,
4-[2-(3-ethyl-2(3H)-benzothiazolylidene)ethylidene]-3-3-phenyl-2-isooxazolin-5-one,
3-(2-benzothiazolyl)-7-(diethylamino)coumarin,
3-(2-benzimidazolyl)-7-(diethylamino)coumarin,
2,3,6,7-tetrahydro-11-oxo-1H,5H,
ethyl 11H-[1]benzopyrano[6,7,8-ij]quinalidine-10-carboxylate,
N,N'-diethylindigo,
thioxoindigo, 2-diemthylaminoanthraquinone,
4-hydroxyazobenzene, and
4-phenylamino-4'-nitroazobenzene, etc.

Other specific examples thereof include benzophenone,
4-methylbenzophenone,
4-dimethylamionobenzophenone,
4,4'-bis(dimethylamino)benzophenone,
4,4'-bis(diethylamino)benzophenone,
2,4-diethylthioxanthone,
2-methylthioxanthone,
isopropylthioxanthone,
anthraquinone,
ethylanthraquinone,
chloroanthraquinone,
hydroxymethylanthraquinone,
aminoanthraquinone,
methylaminoanthraquinone,
aceanthrenequinone,
acenaphthenequinone,
N-methylimidazole,
coumarin,
7-diethylaminocoumarin, and
4-dimethylaminobeozoate.

The compounding amount of the sensitizer in the photopolymerization initiator composition is 5 to 50 mass %.

(2) Photosensitive Composition

The photosensitive composition of the present invention may contain a compound having an ethylenically unsaturated bond and/or a transparent polymer compound, and the above-mentioned photopolymerization initiator composition, and optionally various additives such as a pigment and a solvent.

Usually, photocuring by radical polymerization undergoes polymerization inhibition due to oxygen in the air at the interface with the air so that complete curing becomes difficult. Accordingly, generally photocuring is performed by providing an air-shielding layer such as a cover film lest oxygen should contact the surface or in the presence of an inert gas atmosphere such as argon gas or nitrogen. However, the photosensitive composition of the present invention exhibits sufficient curability regardless of whether or not oxygen is present and thus can be used advantageously in application where use of oxygen-shielding membrane is undesirable, for example, as a photosensitive composition for forming color filters.

By using the thiol compound of the present invention having a so-called branching structure at the α-position and/or β-position in combination with the already-existing photopolymerization initiator in a photosensitive composition, maintenance or improvement of high sensitivity and improvement of storage stability can be achieved mutually compatibly. With the conventional straight chain type thiols (lauryl mercaptan, octanethiol, HSCH$_2$CH$_2$COOH derivatives, etc.) and aromatic thiols such as mercaptobenzothiazole, high sensitivity can be achieved but improvement of storage stability cannot be achieved sufficiently.

The compound having an ethylenically unsaturated bond used in the present invention is a compound generally called monomer or oligomer, which can be cured by a radical polymerization (or crosslinking) reaction. Specific examples thereof include various (meth)acrylates such as (meth) acrylic acid, methyl(meth)acrylate, butyl (meth)acrylate, benzyl(meth)acrylate, 2-hydroxyethyl (meth)acrylate, and 2-hydroxypropyl(meth)acrylate, ethylene glycol di(meth) acrylate, pentaerythritol tri(meth)acrylate, styrene, divinylbenzene, (meth)acrylamide, vinyl acetate, N-hydroxymethyl (meth)acrylamide, dipentaerythritol hexaacrylate, melamine acrylate, and epoxy acrylate prepolymer. Use of polyfunctional (meth)acrylic monomers is preferred in view of exposure sensitivity and various resistances after curing. The compounds having an ethylenically unsaturated bond may be used singly or two or more of them may be used in combination. Note that "(meth)acryl" means both "methacryl" and "acryl".

The polymer compound is capable of forming a uniform film having a thickness of 1 μm or more. Preferably, it is a transparent polymer compound having a transmittance of 80% or more, more preferably 95% or more over the entire region of wavelength 400 to 700 nm in the visible light range. Moreover, the polymer compound which is soluble in developing solutions (solvents or aqueous alkali solutions) is preferred.

Examples of the polymer compound include thermosetting resins, thermoplastic resins and photosensitive resins. For example, polymers and/or copolymers of polyacrylates, poly-α-alkyl acrylates, polyamides, polyvinyl acetals, polyurethanes, polycarbonates, polystyrenes, polyvinyl esters, phenol resins, epoxy resins, novolak resins, alkyd resins, etc. may be used singly or two or more of them may be used as mixtures. The polymer compound may contain ethylenically unsaturated bonds that can be radically polymerized in order to accelerate curing reaction of the photosensitive composition of the present invention or improve the characteristics of cured product. In the case of applications where the cured product remains as a permanent film or in the case where durability is required during the production process, for example, in applications to color filters, treatments at high temperatures or treatments with various solvents or chemicals is performed in downstream operation in the production process. For this reason, it is preferred to use a polymer compound having excellent heat resistance and stability with a lapse of time. The polymer compound of the present invention is compounded in an amount of generally 1 to 300 parts by mass, preferably 50 to 200 parts by mass, per 100 parts by mass of the compound having an ethylenically unsaturated bond.

As the pigments, the following may be mentioned. All of them are indicated by color index number. That is, C. I. Pigment Yellow 12, 13, 14, 17, 20, 24, 55, 83, 86, 93, 109, 110, 117, 125, 137, 139, 147, 148, 153, 154, 166, and 168, C.I. Pigment Orange 36, 43, 51, 55, 59, and 61, C.I. Pigment Red 9, 97, 122, 123, 149, 168, 177, 180, 192, 215, 216, 217, 220, 223, 224, 226, 227, 228, and 240, C. I. Pigment Violet 19, 23, 29, 30, 37, 40, and 50, C. I. Pigment Blue 15, 15:1, 15:4, 15:6, 22, 60, and 64, C. I. Pigment Green 7, 36, C. I. Pigment Brown 23, 25, and 26, C. I. Pigment Black 7, and Titanium Black, and the like may be exemplified. These pigments may be used singly or two or more of them may be used in combination.

Further, according to use of the product, various additives may be added to the photosensitive composition of the present invention in order to impart viscosity operability, characteristics of cured product, and the like. For example, volatile solvents may be added for the purpose of sufficient dispersibility of the components, improvement of operability and adhesion at the time of coating, and adjustment of viscosity. Examples of the volatile solvents include alcohols, ketones and esters. More specifically, they include methanol, ethanol, toluene, cyclohexane, isophorone, cellosolve acetate, diethylene glycol dimethyl ether, ethylene glycol diethyl ether, xylene, ethylbenzene, methyl cellosolve, ethyl cellosolve, butyl cellosolve, propylene glycol monomethyl ether, isoamyl acetate, ethyl lactate, methyl ethyl ketone, acetone, cyclohexanone and the like. These may be used singly or two or more of them may be used as mixtures.

In the case where use of the above-mentioned volatile solvents is difficult, reactive solvents may be used. Examples thereof include 2-hydroxyethyl(meth)acrylate, methyl(meth)acrylate, n-butyl(meth)acrylate, cyclohexyl (meth)acrylate, isobornyl(meth)acrylate, N,N-dimethylaminoethyl (meth)acrylate, N-acryloylmorpholine, N-acryloylpiperidine, N,N-dimethyl(meth)acrylamide, N-vinylpyrrolidone, and N-vinylacetamide. These may be used singly or two or more of them may be used as mixtures. Further, the above-mentioned volatile solvents may be mixed if necessary.

The photosensitive composition of the present invention may further contain fluorescent whiteners, surfactants, plasticizers, flame-retardants, antioxidants, UV absorbents, foaming agents, fungicides, antistatic agents, magnetic materials, electrically conductive materials, antimicrobial/bactericidal agents, porous adsorbents, perfumes, and the like, depending on the purpose. Also, the photosensitive composition of the present invention may contain heat polymerization inhibitors in order to prevent polymerization during storage. Specific examples of the heat polymerization inhibitor include p-methoxyphenol, hydroquinone, catechol, tert-butylcatechol, phenothiazine, and methoquinone.

To prevent the occurrence of gelling by polymerization reaction or the like at the time of dispersing, polymerization inhibitors may be added. To disperse pigments well, dispersant may be added as appropriate. The dispersant has the effects of helping pigments to be dispersed and of preventing reagllomeration after the dispersion. For the purpose of obtaining appropriate flowability or obtaining light-shielding property, mechanical and physical characteristics of the cured product, barium sulfate, calcium carbonate, silica, titania, alumina, aluminum powder and the like extender pigments may be added.

The compounding ratio of each component in the photosensitive composition of the present invention is not generally prescribed but usually it is as follows.

In the case where the compound having an ethylenically unsaturated bond and the polymer compound are used in combination, the compounding amount of the polymer compound is generally 1 to 300 parts by mass, preferably 50 to 200 parts by mass, per 100 parts by mass of the compound having an ethylenically unsaturated bond.

The compounding amount of the photopolymerization initiator composition is generally 2 to 400 parts by mass, preferably 20 to 200 parts by mass, per 100 parts by mass of the compound having an ethylenically unsaturated bond.

More specifically, it is preferred that the components be compounded such that the thiol compound in the photopolymerization initiator composition is in an amount of generally 1 to 200 parts by weight, preferably 10 to 100 parts by mass, per 100 parts by mass of the compound having an ethylenically unsaturated bond. If the amount of thiol compound is too small, initiation of polymerization may in some cases proceed only inefficiently while if the amount is too large, no further improvement in polymerization initiation function is expected and in addition the thiol compound may give an adverse influence on the physical properties of the cured product, so that both the cases are not preferable.

It is preferred that the components be compounded such that the sensitizer in the photopolymerization initiator composition is present in an amount of generally 1 to 60 parts by mass, preferably 2 to 30 parts by mass, per 100 parts by mass of the compound having an ethylenically unsaturated bond. If the amount of the sensitizer is too small, it may occur in some cases that no sensitizing effect is obtained while if the amount is too large, it may in some cases occur that the light transmission efficiency is decreased due to light absorption thereby and the polymerization initiation efficiency may be decreased, so that both the cases are not preferable.

The compounding amount of the pigment is generally 100 to 2,000 parts by mass per 100 parts by mass of the compound having an ethylenically unsaturated bond.

The photosensitive composition of the present invention can be produced by mixing the above-mentioned components by means of various kinds of dispersing means such as a three-roll mill, a two-roll mill, a sand mill, an attritor, a ball mill, a kneader, and a paint shaker. The monomer and photopolymerization initiator may be compounded after the pigment is dispersed.

The photosensitive composition of the present invention may be coated on substrates, for example those made of glass, aluminum, or a film of polyester such as polyethylene terephthalate (PET) by a coating method such as spray coating, spinner coating, roll coating, screen coating, spread coating, dip coating, or calendar coating. Here in order to obtain appropriate coating characteristics, a small amount of silicone- or fluorine-contained surfactant as a leveling agent or defoaming agent may be added to the photosensitive composition of the present invention. The coated photosensitive composition is dried by a hot-air oven or a hot plate generally under conditions of 60 to 100° C. for 10 to 30 minutes to evaporate the volatile solvent. If the temperature in this instance is too high or the heating time is too long, polymerization or crosslinking partially occurs, so that the solubility of an unexposed portion in the developer is decreased to cause so-called burn, which is undesirable. Drying may be performed under reduced pressure. Thereafter, an oxygen-shielding membrane may be provided on the coating film, depending on the purpose.

The dried coating film is exposed to light. On this occasion, exposure to UV light through a photomask having a pattern may be performed depending on the application. As the light source, generally super-high pressure mercury lamp, metal halide lamp, xenon lamp and the like are used. Dependent on the application or the kind of substrate, filters having a heat ray cutting property or wavelength selectivity may be used. By removing uncured portion after the exposure, a pattern can be formed on the substrate.

The method of forming a pattern of a certain configuration with the photosensitive composition of the present invention is roughly classified into two types. One is a method of coating the photosensitive composition in a desired configuration and then curing it by irradiation of light. The other is a method of coating the photosensitive composition evenly on a substrate, irradiating light to the photosensitive composition so that the exposed portion forms a desired configuration to cure it, and then removing an unexposed portion by means such as washing, peeling, physical polishing, chemical polishing or the like to form a pattern with the photocured product. The pattern formed with the photosensitive composition of the present invention means a photocured product of the photosensitive composition formed on a substrate so as to have a certain configuration. Specific examples thereof include patterns in the field of applications to resists for optical plate making, solder resists, etching resists, color filter resists, holograms, optical sculpturing, and UV ink. The photosensitive composition of the present invention is particularly suitable for development-type resists that form precise patterns.

For the substrate used in the pattern formation of the present invention, inorganic materials such as glass and silicon, metallic materials such as aluminum, stainless steel, and copper, resin materials such as PET, polyester, polyimide, epoxy resin, polyethylene, and polycarbonate and in addition, paper may be used. The surface of the substrates may be subjected to oxidation treatment, acid treatment, plasma treatment, discharge treatment or the like to improve adhesion of the photosensitive composition. Since the photosensitive composition is present on the surface of a substrate, the thickness of the substrate can be set optionally. A resin layer or the like that does not participate in the photoreaction may be provided between the photosensitive composition and the substrate.

In the above-mentioned pattern formation, when the uncured portion of the photosensitive composition after the exposure to light is dissolved and removed, examples of the solvent for the developer include organic solvents such as N-methylpyrrolidone, methanol, ethanol, toluene, cyclohexane, isophorone, cellosolve acetate, diethylene glycol dimethyl ether, ethylene glycol diethyl ether, xylene, ethylbenzene, methyl cellosolve, ethyl cellosolve, butyl cellosolve, propylene glycol monomethyl ether, propylene glycol monomethyl ether acetate, isoamyl acetate, ethyl lactate, methyl ethyl ketone, acetone, cyclohexanone, N,N-dimethylformamide, and acetonitrile as well as aqueous alkali solutions. These may be used singly or two or more of them may be used in combination. Further, basic substances such as trimethylamine and triethylamine and surfactants may be added to these solvents.

As the aqueous alkali solution, aqueous solutions of inorganic salts such as, for example, sodium hydroxide, potassium hydroxide, sodium carbonate, and potassium carbonate, aqueous solutions of organic salts such as hydroxytetramethylammonium and hydroxytetraethylammonium may be added. These may also be used singly or two or more of them may be used in combination.

BEST MODE FOR CARYING OUT THE INVENTION

Hereinafter, the present invention will be described based on examples. However, the present invention should not be considered as being limited by the examples. In the examples, "part" means part by mass, and "%" means % by mass.

Synthetic Example 1

Synthesis of Ethylene Glycol bis(3-mercaptobutyrate) (EGMB)

In a 200-ml eggplant-shaped flask were charged 3.72 g (60 mmol) of ethylene glycol (manufactured by Wako Pure Chemical Industry Co., Ltd.), 15.86 g (132 mmol) of 3-mercaptobutanoic acid (manufactured by Yodo Chemical Co., Ltd.), 0.92 g (4.8 mmol) of p-toluenesulfonic acid monohydrate (manufactured by Junsei Chemicals Co., Ltd.), and 60 g of toluene (manufactured by Junsei Chemicals Co., Ltd.), and a Dean-Stark apparatus and a condenser tube were equipped thereto. While the contents being stirred, they were heated at an oil bath temperature of 140° C. After 2 hours from the start of the reaction, 0.92 g (4.8 mmol) of p-toluenesulfonic acid monohydrate was added and further after 4 hours from the start of the reaction, 0.46 g (2.4 mmol) of p-toluenesulfonic acid monohydrate was added. Further, after the reaction was performed for another 1 hour, the reaction mixture was left to cool and neutralized with 200 ml of an aqueous 10% sodium-hydrogen carbonate solution. Further, the reaction mixture was washed with deionized water three times, and then dehydrated and dried over anhydrous magnesium sulfate (manufactured by Junsei Chemicals Co., Ltd.). Then, the toluene was distilled off and the residue was subjected to column chromatography with silica gel to purify EGMB. The silica gel used was Wako Gel C-200 (manufactured by Wako Pure Chemical Industry Co., Ltd.), and n-hexane/ethyl acetate=6/1 (by volume ratio) was used as an elution solvent. The EGMB obtained by the purification was a colorless transparent liquid and the yield was 7.57 g (45%). The EGMB had a compositional formula of $C_{10}H_{18}O_4S_2$ and a molecular weight of 266.38.

Synthetic Example 2

Synthesis of 1,2-Propylene Glycol bis(3-mercaptobutyrate) (PGMB)

In a 100-ml eggplant-shaped flask were charged 3.04 g (40 mmol) of 1,2-propylene glycol (manufactured by Wako Pure Chemical Industry Co., Ltd.), 10.57 g (88 mmol) of 3-mercaptobutanoic acid, 0.61 g (3.2 mmol) of p-toluenesulfonic acid monohydrate, and 40 g of toluene, and a Dean-Stark apparatus and a condenser tube were equipped thereto. While the contents being stirred, they were heated at an oil bath temperature of 140° C. After 2 hours from the start of the reaction, 0.61 g (3.2 mmol) of p-toluenesulfonic acid monohydrate was added, and after 4 hours from the start of the reaction, 0.30 g (1.6 mmol) of p-toluenesulfonic acid monohydrate was added. Further, after the reaction was performed for another 1 hour, the reaction mixture was left to cool and neutralized with 100 ml of an aqueous 10% sodium hydrogen carbonate solution. Further, the reaction mixture was washed with deionized water three times, and then dehydrated and dried over anhydrous magnesium sulfate (manufactured by Junsei Chemicals Co., Ltd.). Then, the toluene was distilled off and the residue was subjected to column chromatography with silica gel to purify PGMB. The silica gel used was Wako Gel C-200, and n-hexane/ethyl acetate=6/1 (by volume ratio) was used as an elution solvent. The PGMB obtained by the purification was a colorless transparent liquid and the yield was 2.80 g (25%). The PGMB had a compositional formula of $C_{11}H_{20}O_4S_2$ and a molecular weight of 280.41.

Synthetic Example 3

Synthesis of Trimethylolpropane tris(3-mercaptobutyrate) (TPMB)

In a 100-ml eggplant-shaped flask were charged 2.68 g (20 mmol) of trimethylolpropane (manufactured by Tokyo Kasei Kogyo Co., Ltd.), 7.57 g (63 mmol) of 3-mercaptobutanoic acid, 0.23 g (1.2 mmol) of p-toluenesulfonic acid monohydrate, and 20 g of toluene, and a Dean-Stark apparatus and a condenser tube were equipped thereto. While the contents being stirred, they were heated at an oil bath temperature of 145° C. After 3 hours from the start of the reaction, the reaction mixture was left to cool and neutralized with 50 ml of an aqueous 5% sodium hydrogen carbonate solution. Further, the reaction mixture was washed with deionized water two times, and then dehydrated and dried over anhydrous magnesium sulfate. Then, the toluene was distilled off and the residue was subjected to column chromatography with silica gel to purify TPMB. The silica gel used was Wako Gel C-200, and n-hexane/ethyl acetate=5/1 (by volume ratio) was used as an elution solvent. The TPMB obtained by the purification was a colorless transparent liquid and the yield was 5.63 g (64%). The TPMB had a compositional formula of $C_{18}H_{32}O_6S_3$ and a molecular weight of 440.64.

Synthetic Example 4

Synthesis of Ethylene Glycol bis(2-mercaptoisobutyrate) (EGMIB)

In a 200-ml eggplant-shaped flask were charged 3.72 g (60 mmol) of ethylene glycol, 15.86 g (132 mmol) of 2-mercaptoisobutanoic acid (manufactured by Yodo Chemical Co., Ltd.), 0.92 g (4.8 mmol) of p-toluenesulfonic acid monohydrate, and 60 g of toluene, and a Dean-Stark apparatus and a condenser tube were equipped thereto. While the contents being stirred, they were heated at an oil bath temperature of 140° C. After 2 hours from the start of the reaction, 0.92 g (4.8 mmol) of p-toluenesulfonic acid monohydrate was added, and after 5 hours from the start of the reaction, 0.46 g (2.4 mmol) of p-toluenesulfonic acid monohydrate was added. Further, after the reaction was performed for another 2 hours, the reaction mixture was left to cool and neutralized with 200 ml of an aqueous 10% sodium hydrogen carbonate solution. Further, the reaction mixture was washed with deionized water three times, and then dehydrated and dried over anhydrous magnesium sulfate. Then, the toluene was distilled off and the residue was subjected to column chromatography with silica gel to purify EGMIB. The silica gel used was Wako Gel C-200 (manufactured by Wako Pure Chemical Industry Co., Ltd.), and n-hexane/ethyl acetate=6/1 (by volume ratio) was used as an elution solvent. The EGMIB obtained by the purification was a white crystal and the yield was 6.08 g (38%). The EGMIB had a compositional formula of $C_{10}H_{18}O_4S_2$ and a molecular weight of 266.38.

Synthetic Example 5

Synthesis of 1,2-propylene Glycol bis(2-mercaptoisobutyrate) (PGMIB)

In a 200-ml eggplant-shaped flask were charged 4.57 g (60 mmol) of 1,2-propylene glycol, 15.86 g (132 mmol) of 2-mercaptoisobutanoic acid, 1.20 g (6.3 mmol) of p-toluenesulfonic acid monohydrate, and 100 g of methylene chloride (manufactured by Junsei Chemicals Co., Ltd.), and a Soxhlet extractor which was loaded with Molecular sieves 4A (manufactured by UNION SHOWA K.K.) and a condenser tube were equipped thereto. While the contents being stirred, they were heated at an oil bath temperature of 70° C. After the reaction was performed for 30 hours, the reaction mixture was neutralized with 200 ml of an aqueous 10% sodium hydrogen carbonate. Further, the reaction mixture was washed with deionized water three times, and then dehydrated and dried over anhydrous magnesium sulfate. Then, the methylene chloride was distilled off and the residue was subjected to column chromatography with silica gel to purify PGMIB. The silica gel used was Wako Gel C-200, and n-hexane/ethyl acetate=6/1 (by volume ratio) was used as an elution solvent. The PGMIB obtained by the purification was a colorless transparent liquid and the yield was 4.00 g (24%). The PGMIB had a compositional formula of $C_{11}H_{20}O_4S_2$ and a molecular weight of 280.41.

Synthetic Example 6

Synthesis of Trimethylolpropane tris(2-mercaptoisobutyrate) (TPMIB)

In a 100-ml eggplant-shaped flask were charged 2.68 g (20 mmol) of trimethylolpropane (manufactured by Tokyo Kasei Kogyo Co., Ltd.), 7.57 g (63 mmol) of 2-mercaptoisobutanoic acid, 0.23 g (1.2 mmol) of p-toluenesulfonic acidmonohydrate, and 20 g of toluene, and a Dean-Stark apparatus and a condenser tube were equipped thereto. While the contents being stirred, they were heated at an oil bath temperature of 145° C. After 3 hours from the start of the reaction, the reaction mixture was left to cool and neutralized with 50 ml of an aqueous 5% sodium hydrogen carbonate solution. Further, the reaction mixture was washed with deionized water two times, and then dehydrated and dried over anhydrous magnesium sulfate. Then, the toluene was distilled off and the residue was subjected to column chromatography with silica gel to purify TPMIB. The silica gel used was Wako Gel C-200, and n-hexane/ethyl acetate=5/1 (by volume ratio) was used as an elution solvent. The TPMIB obtained by the purification was a white crystal and the yield was 4.50 g (51%). The TPMIB had a compositional formula of $Cl_{18}H_{32}O_6S_3$ and a molecular weight of 440.64.

Structural Analysis;

(1) EGMB $^1$H-NMR

FIG. 1 shows a $^1$H-NMR chart of EGMB. Measurement by $^1$H-NMR was performed in deuterated chloroform by using AMX400 manufactured by Bruker Co.

$^{13}$C-NMR

Figure 2:
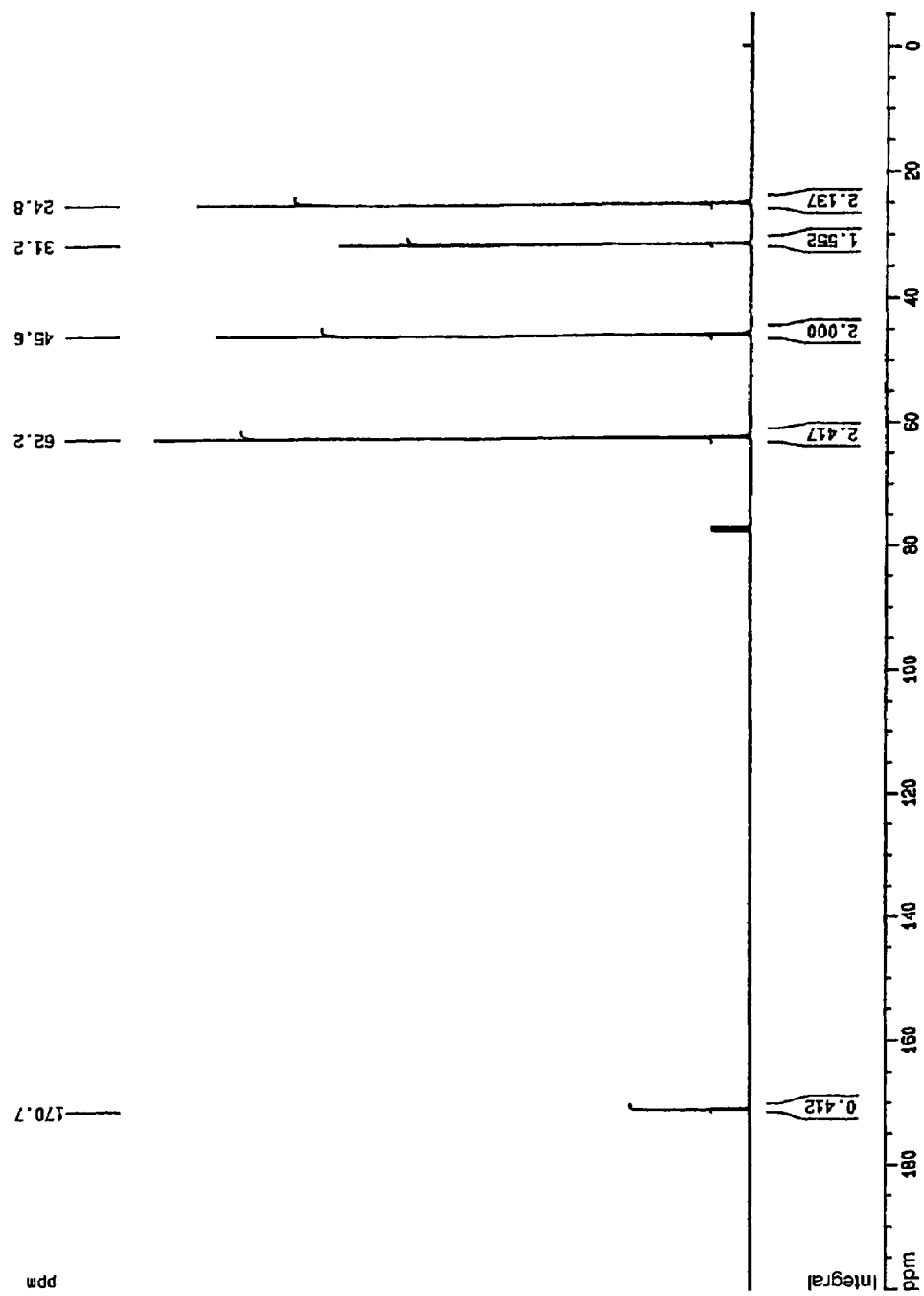

FIG. 2 shows a $^{13}$C-NMR chart of EGMB. Measurement by $^{13}$C-NMR was performed in deuterated chloroform by using AMX400 manufactured by Bruker Co. and assignment of the peak of each chemical shift was performed.

$$H_3\overset{1}{C}-\overset{\overset{2}{H}}{\underset{SH}{C}}-\overset{3}{\underset{H_2}{C}}-\overset{4}{\underset{\parallel}{C}}-O-\overset{5}{\underset{H_2}{C}}-\overset{6}{\underset{H_2}{C}}-O-\overset{4'}{\underset{\parallel}{C}}-\overset{3'}{\underset{H_2}{C}}-\overset{\overset{2'}{H}}{\underset{SH}{C}}-\overset{1'}{C}H_3$$

EGMB

Ethylene Glycol bis(3-mercaptobutyrate)

24.8 ppm: Carbon atoms of 1- and 1'-methyl groups
31.2 ppm: Carbon atoms of 2- and 2'-methine groups
45.6 ppm: Carbon atoms of 3- and 3'-methylene groups
62.2 ppm: Carbon atoms of 5- and 6-methylene groups
170.7 ppm: Carbon atoms of 4- and 4'-carbonyl groups Mass Spectrometry For the mass spectrometry of EGMB, measurements were performed by using JMS-SX 102A manufactured by JEOL. Ltd. The peak corresponding to MH$^+$ was detected at the position of m/z=267, which coincided with the molecular weight of EGMB being 266.38.

Figure 3:
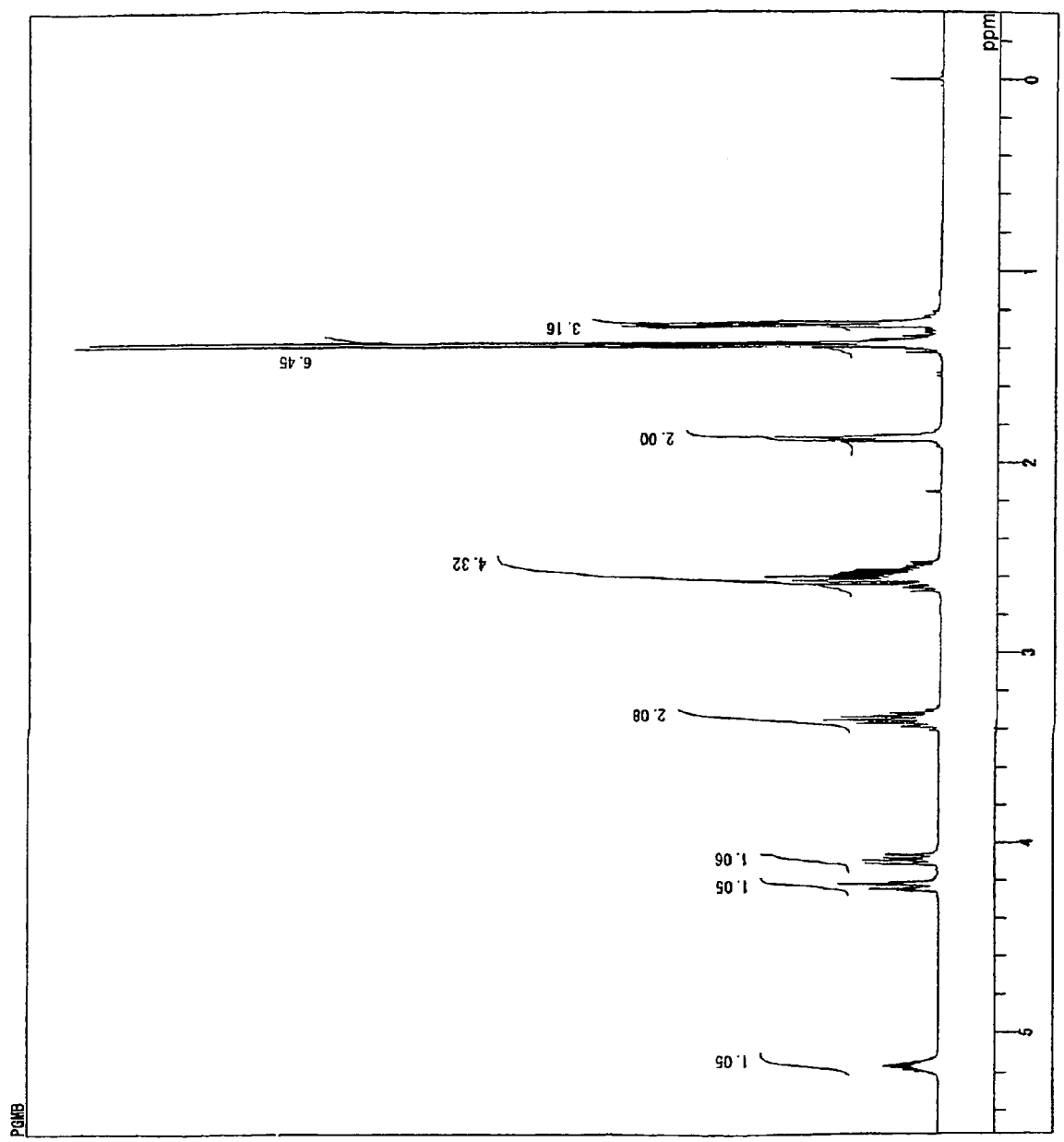
FIG. 3 and FIG. 4 are diagrams showing a $^1$H-NMR spectrum and $^{13}$C-NMR spectrum of 1,2-propylene glycol bis(3-mercaptobutyrate) (PGMB)

(2) PGMB $^1$H-NMR $^1$H-NMR of PGMB was measured in deuterated chloroform by using JNM-AL400 manufactured by JEOL. Ltd. The results obtained are shown in FIG. 3.

Figure 4:
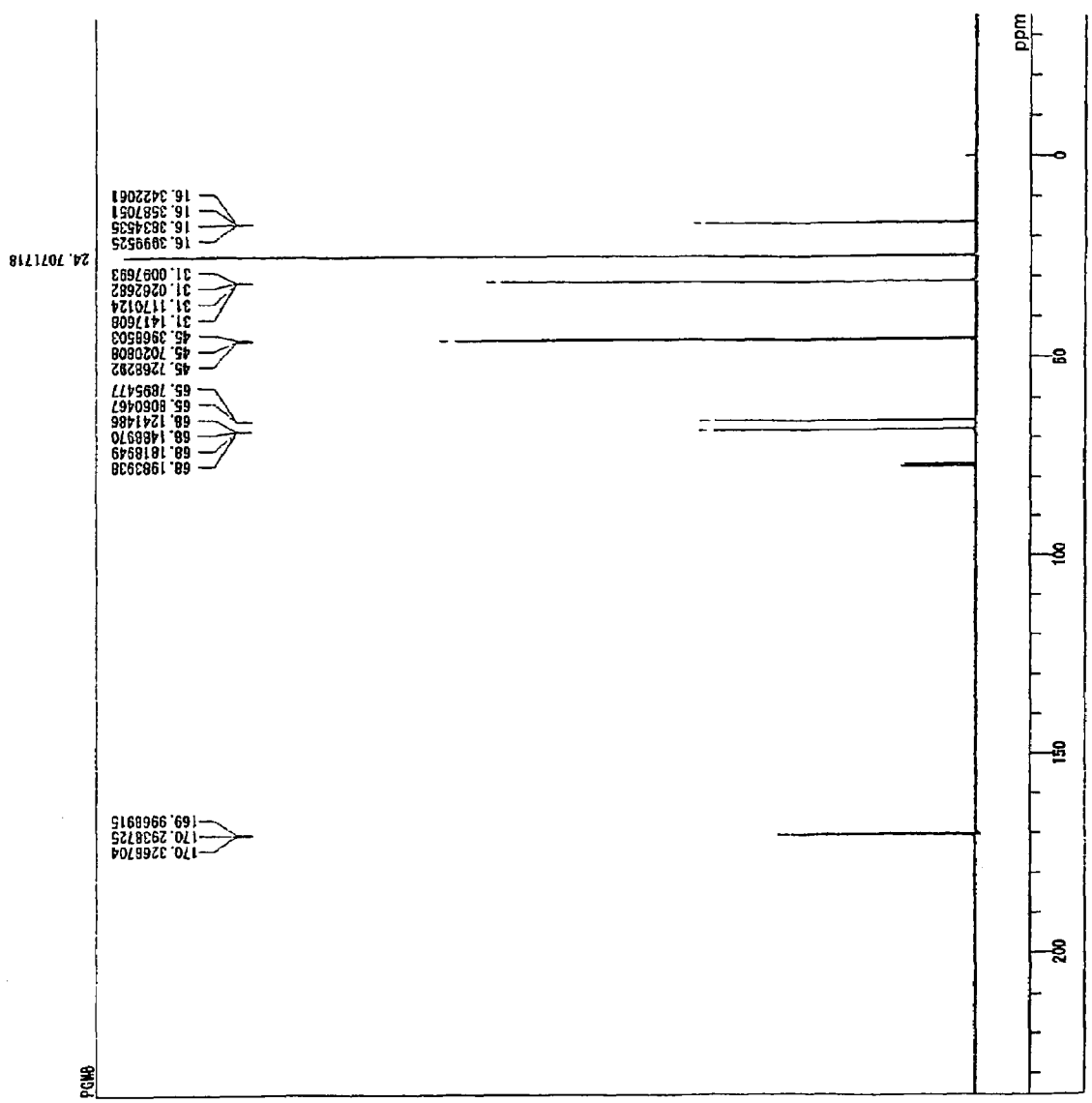

$^{13}$C-NMR $^{13}$C-NMR of PGMB was measured in deuterated chloroform by using JNM-AL400 manufactured by JEOL. Ltd. and assignment of the peak of each chemical shift was performed. The results obtained are shown in FIG. 4.

$$H_3\overset{1}{C}-\overset{\overset{2}{H}}{\underset{SH}{C}}-\overset{3}{\underset{H_2}{C}}-\overset{4}{\underset{\parallel}{C}}-O-\overset{\overset{5}{H}}{\underset{\underset{7}{CH_3}}{C}}-\overset{6}{\underset{H_2}{C}}-O-\overset{4'}{\underset{\parallel}{C}}-\overset{3'}{\underset{H_2}{C}}-\overset{\overset{2'}{H}}{\underset{SH}{C}}-\overset{1'}{C}H_3$$

PGMB

Propylene Glycol bis(3-mercaptobutyrate)

16.4 ppm: Carbon atom of 7-methyl group
24.7 ppm: Carbon atoms of 1- and 1'-methyl groups
31.1 ppm: Carbon atoms of 2- and 2'-methine groups 45.4, 45.7 ppm: Carbon atoms of 3- and 3'-methylene groups
65.8 ppm: Carbon atom of 6-methylene group
68.2 ppm: Carbon atom of 5-methine group
170.0, 170.3 ppm: Carbon atoms of 4- and 4'-carbonyl groups Mass Spectrometry For the mass spectrometry of PGMB, measurements were performed by using the same apparatus as that for EGMB. The peak corresponding to $MH^+$ was detected at the position of m/z=281, which coincided with the molecular weight of PGMB being 280.41.

Figure 5:
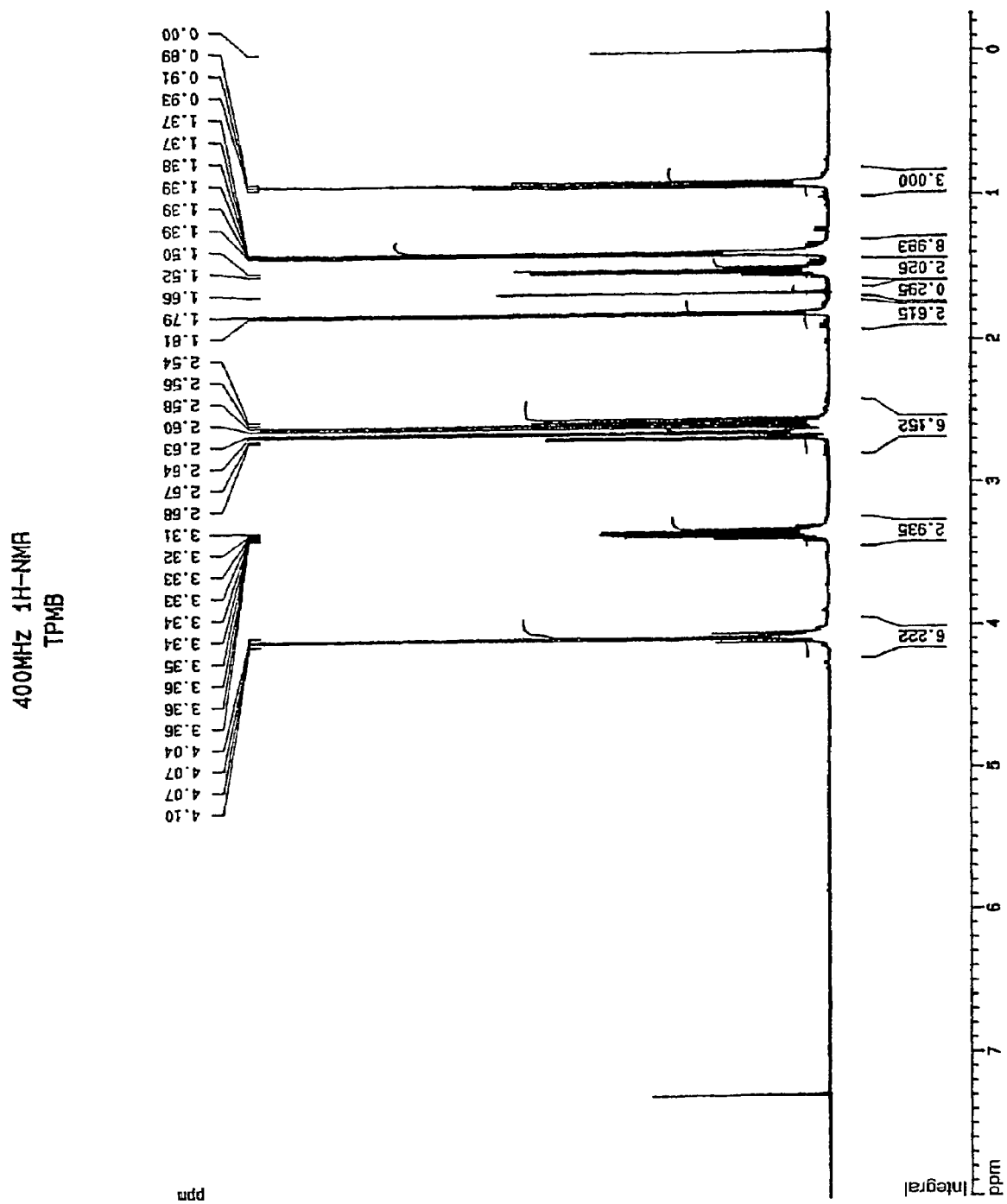
FIG. 5 and FIG. 6 are diagrams showing a $^1$H-NMR spectrum and $^{13}$C-NMR spectrum of trimethylolpropane tris(3-mercaptobutyrate) (TPMB)

(3) TPMB $^1$H-NMR $^1$H-NMR of TPMB was measured in deuterated chloroform by using the same apparatus as that for EGMB. The results obtained are shown in FIG. 5.

Figure 6:
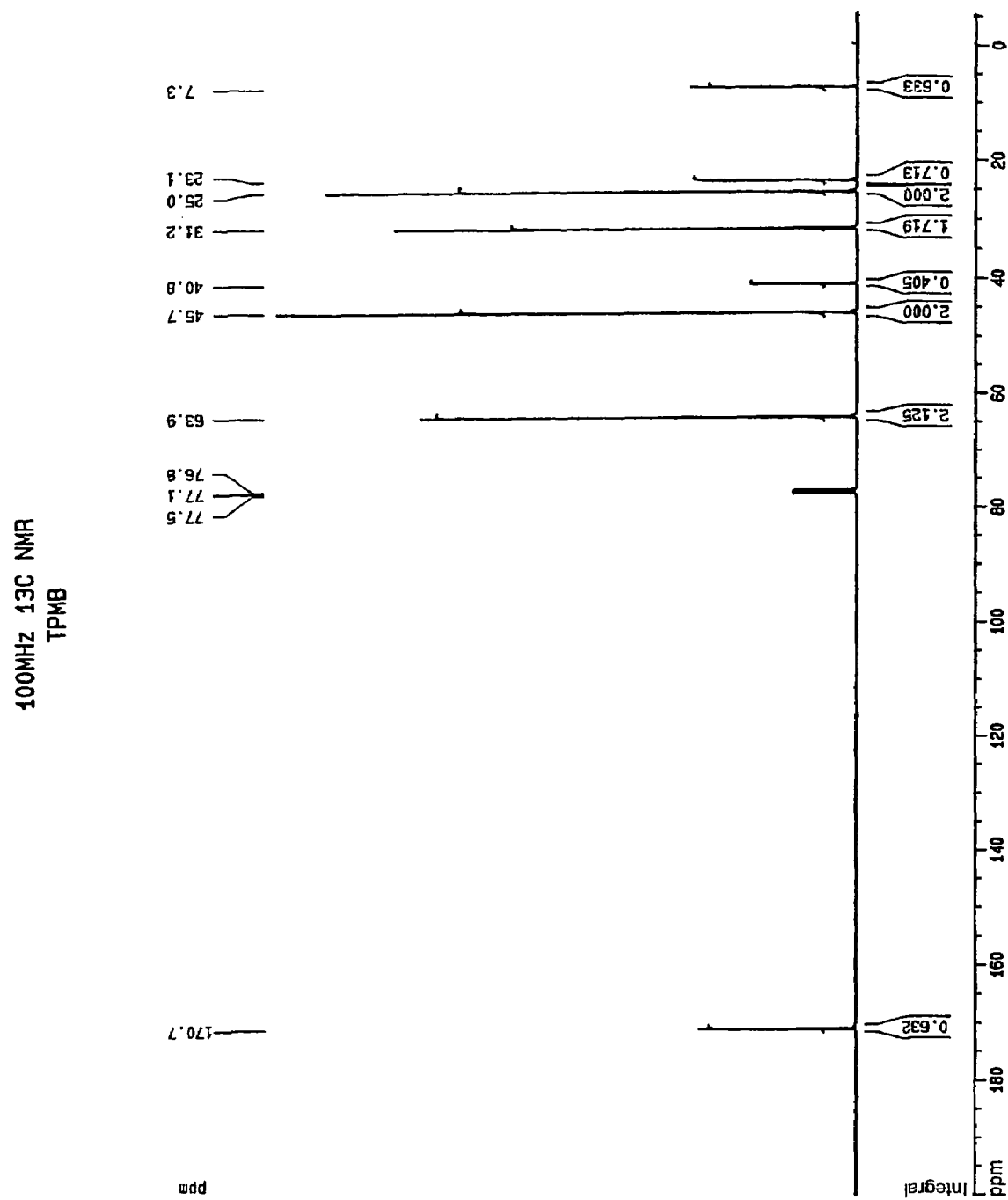

$^{13}$C-NMR $^{13}$C-NMR of TPMB was measured in deuterated chloroform by using the same apparatus as that for EGMB and assignment of the peak of each chemical shift was performed. The results obtained are shown in FIG. 6.

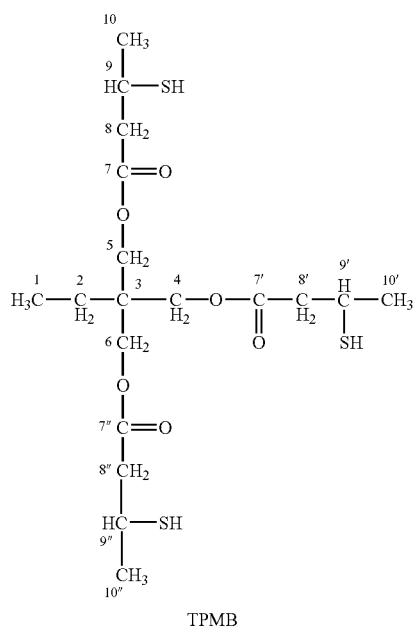

TPMB

Trimethylolpropane tris(3-mercaptobutyrate)

7.3 ppm: Carbon atom of 1-methyl group
23.1 ppm: Carbon atom of 2-methylene group
25.0 ppm: Carbon atoms of 10-, 10'-, and 10"-methyl groups
31.2 ppm: Carbon atoms of 9-, 9'-, and 9"-methine groups
40.8 ppm: 3-Quaternary carbon atom
45.7 ppm: Carbon atoms of 8-, 8'- and 8"-methylene groups
63.9 ppm: Carbon atoms of 4-, 5-, and 6-methylene groups
170.7 ppm: Carbon atoms of 7-, 7'-, and 7"-carbonyl groups Mass Spectrometry For the mass spectrometry of TPMB, measurements were performed by using the same apparatus as that for EGMB. The peak corresponding to $MH^+$ was detected at the position of m/z=441, which coincided with the molecular weight of TPMB being 440.64.

Figure 7:
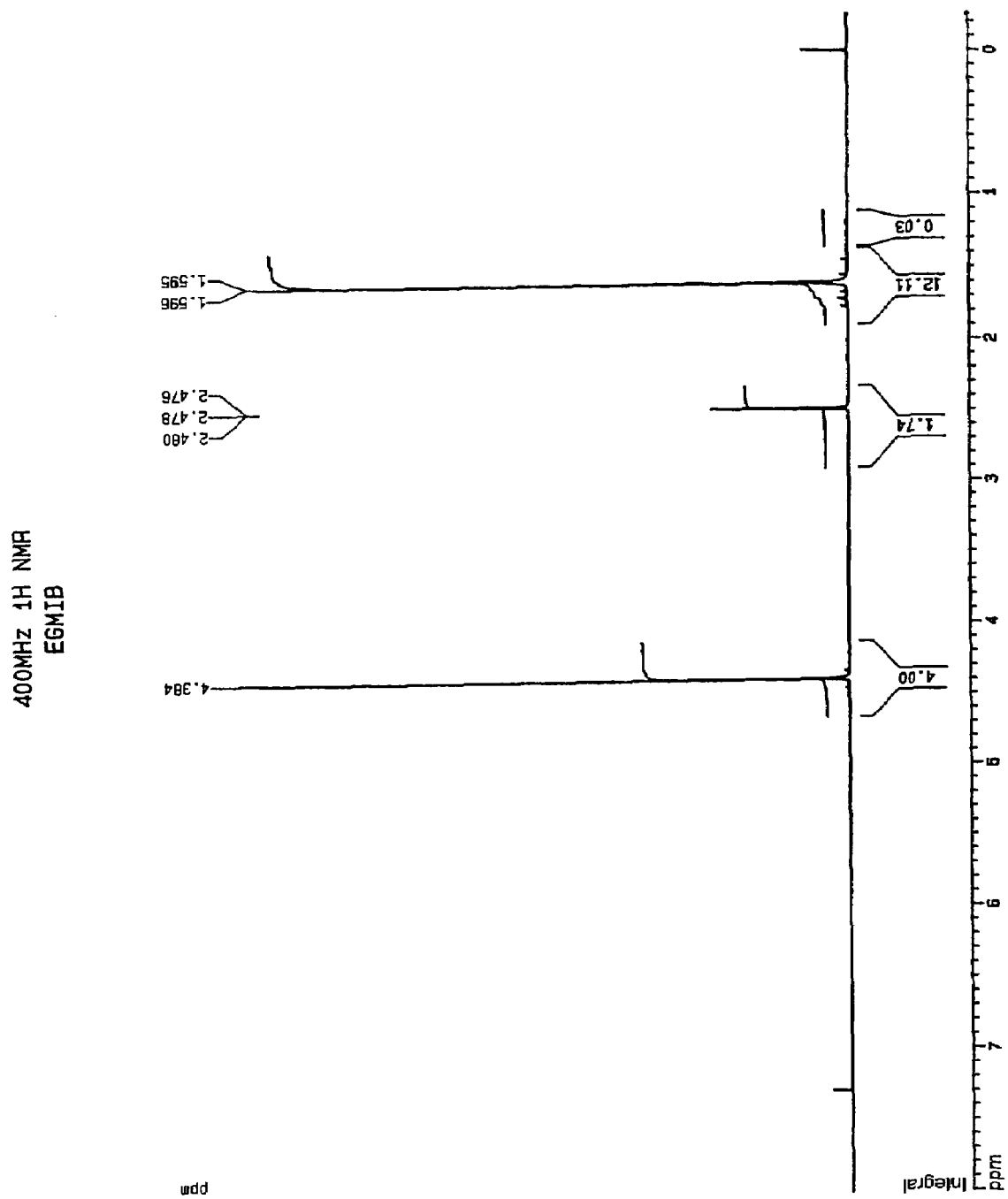
FIG. 7 and FIG. 8 are diagrams showing a $^1$H-NMR spectrum and $^{13}$C-NMR spectrum of ethylene glycol bis(2-mercaptoisobutyrate) (EGMIB)

(4) EGMIB $^1$H-NMR $^1$H-NMR of EGMIB was measured in deuterated chloroform by using the same apparatus as that for EGMB. The results obtained are shown in FIG. 7.

Figure 8:
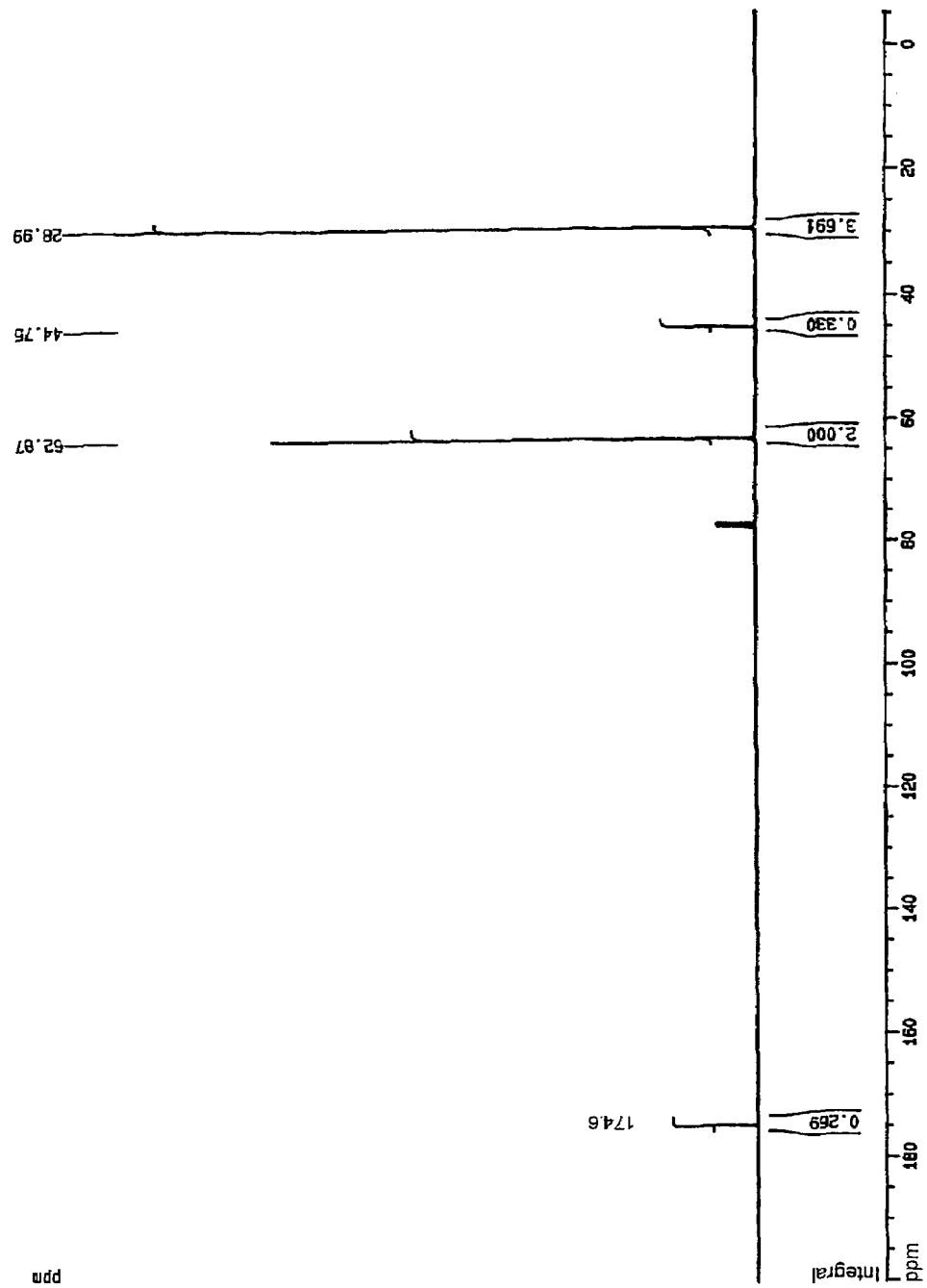

$^{13}$C-NMR $^{13}$C-NMR of EGMIB was measured in deuterated chloroform by using the same apparatus as that for EGMB and assignment of the peak of each chemical shift was performed. The results obtained are shown in FIG. 8.

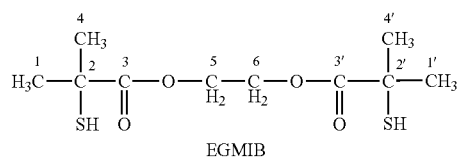

EGMIB

Ethylene glycol bis(2-mercaptoisobutyrate)

29.0 ppm: Carbon atoms of 1-, 1'-, 4- and 4'-methyl groups
44.8 ppm: 2- and 2'-quarternary carbon atoms
62.9 ppm: Carbon atoms of 5- and 6-methylene groups
174.6 ppm: Carbon atoms of 3- and 3'-carbonyl groups Mass Spectrometry For the mass spectrometry of EGMIB, measurements were performed by using the same apparatus as that for EGMB. The peak corresponding to $MH^+$ was detected at the position of m/z=267, which coincided with the molecular weight of EGMIB being 266.38.

Melting Point:

Melting point was measured by using a melting point measuring apparatus type 510, manufactured by BUCHI Co. The melting point measured was 38° C.

Figure 9:
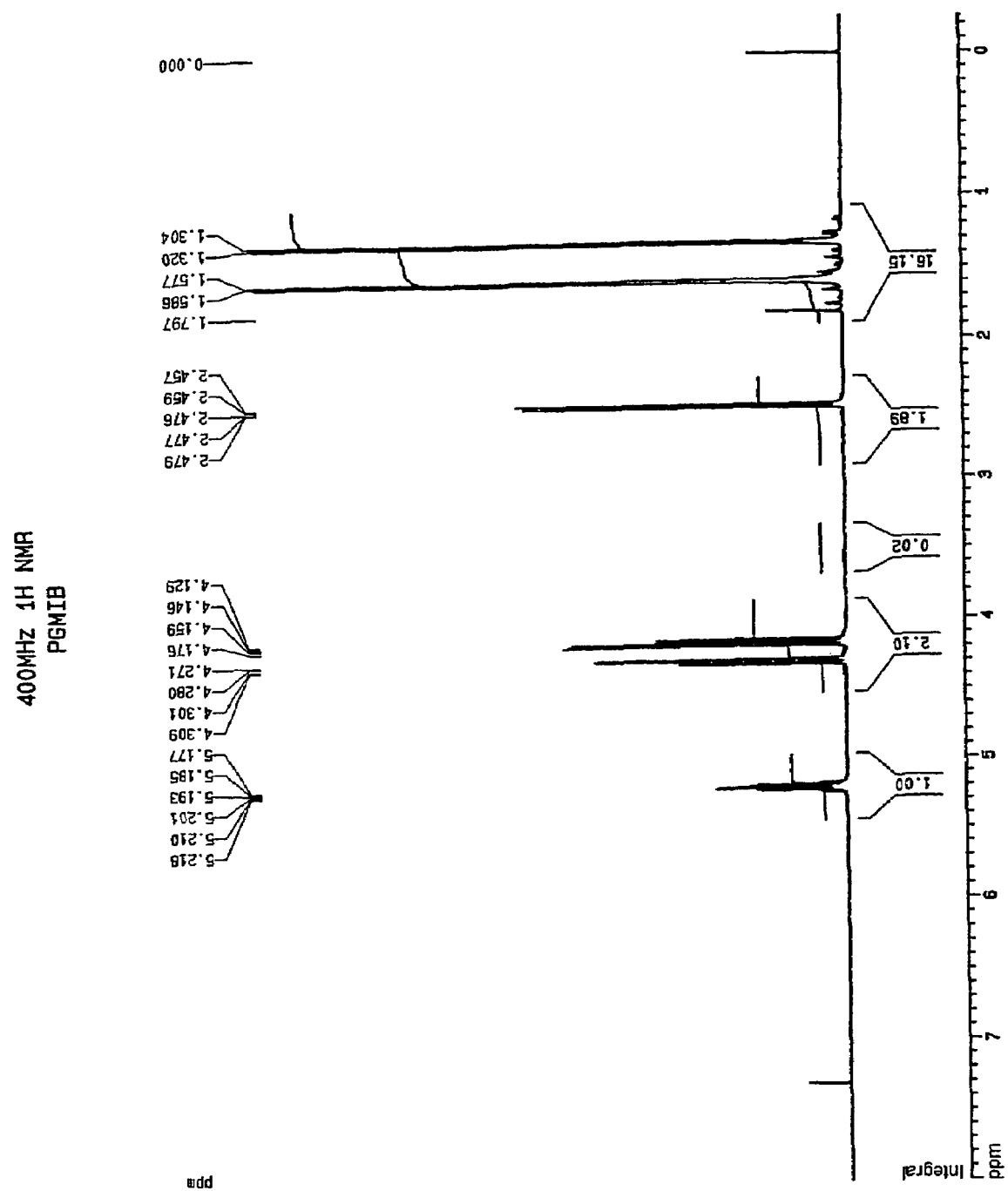
FIG. 9 and FIG. 10 are diagrams showing a $^1$H-NMR spectrum and $^{13}$C-NMR spectrum of 1,2-propylene glycol bis(2-mercaptoisobutyrate) (PGMIB)

(5) PGMIB $^1$H-NMR $^1$H-NMR of PGMIB was measured in deuterated chloroform by using the same apparatus as that for EGMB. The results obtained are shown in FIG. 9.

Figure 10:
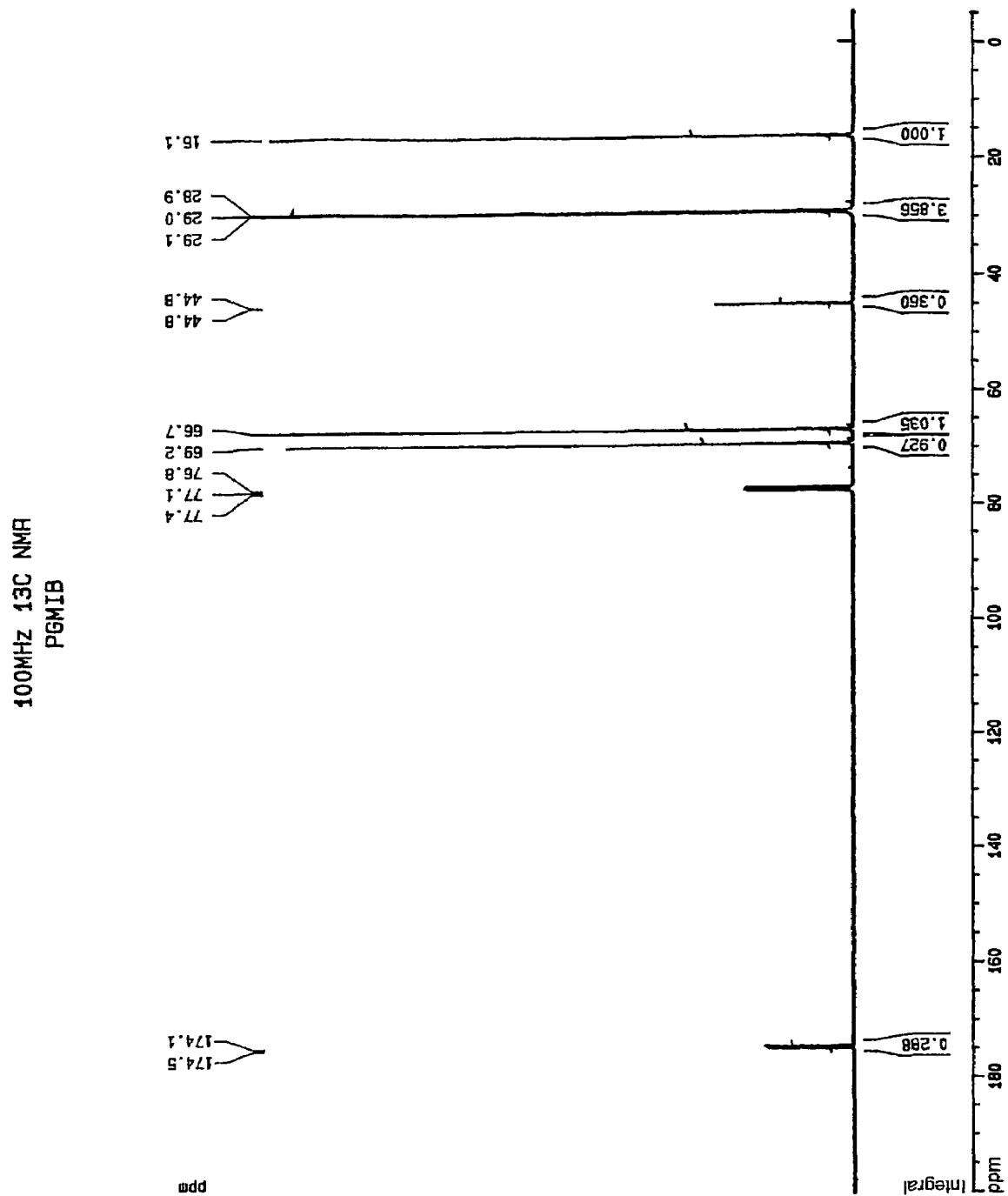

$^{13}$C-NMR $^{13}$C-NMR of PGMIB was measured in deuterated chloroform by using the same apparatus as that for EGMB and assignment of the peak of each chemical shift was performed. The results obtained are shown in FIG. 10.

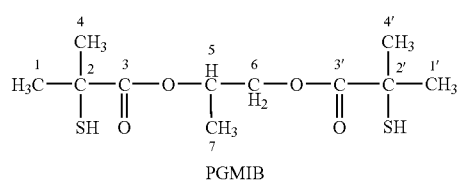

PGMIB

Propylene glycol bis(2-mercaptoisobutyrate)

| | |
|---|---|
| 16.1 ppm: | Carbon atom of 7-methyl group |
| 29.0 ppm: | Carbon atoms of 1-, 1'-, 4- and 4'-methyl groups |
| 44.8 ppm: | 2- and 2'- quarternary carbon atoms |
| 66.7 ppm: | Carbon atom of 6-methylene group |
| 69.2 ppm: | Carbon atom of 5-methine group |
| 174.1, 174.5 ppm: | Carbon atoms of 3- and 3'-carbonyl groups |

Mass Spectrometry

For the mass spectrometry of PGMIB, measurements were performed by using the same apparatus as that for EGMB. The peak corresponding to $MH^+$ was detected at the position of m/z=281, which coincided with the molecular weight of PGMIB being 280.41.

Figure 11:
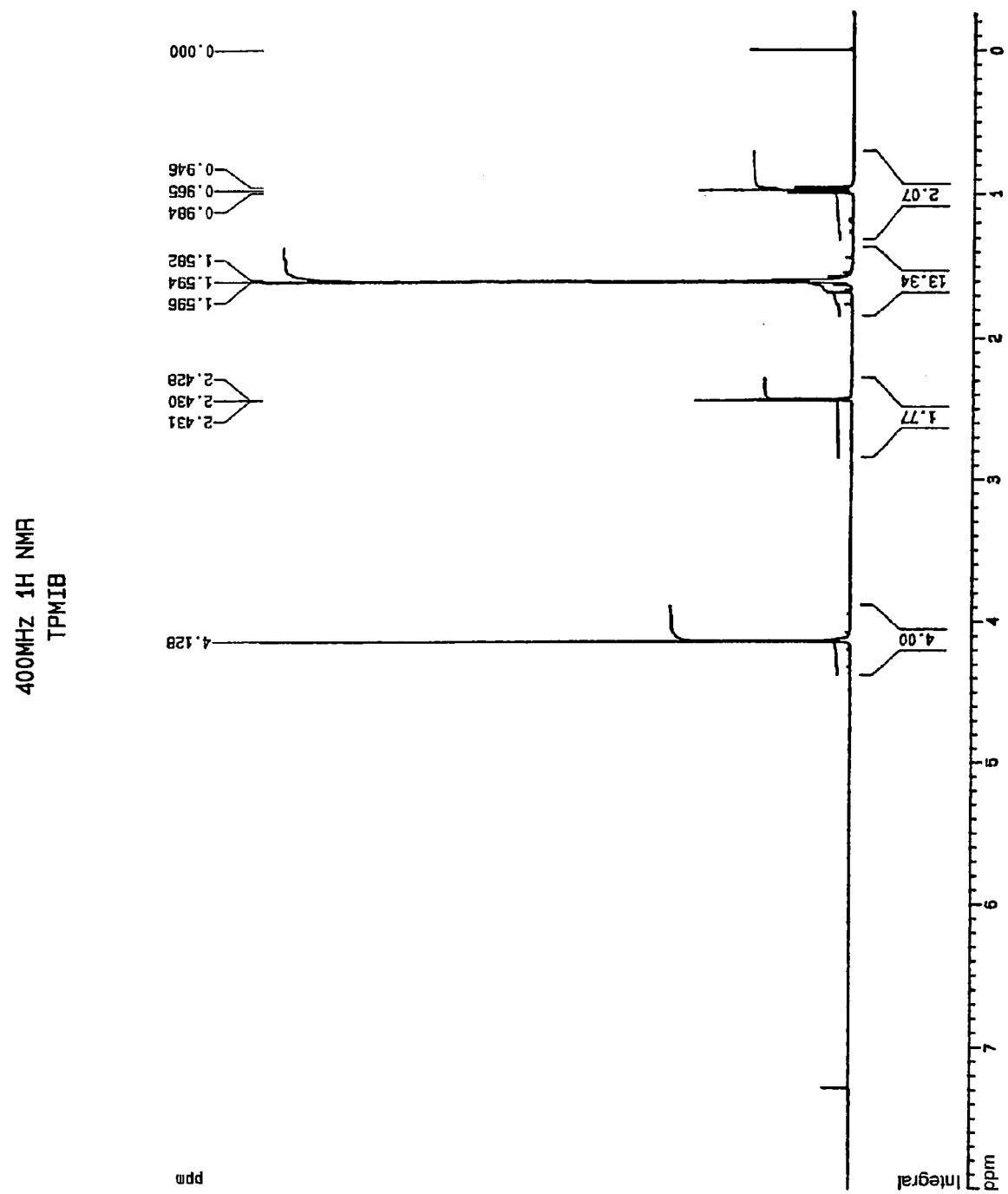
FIG. 11 and FIG. 12 are diagrams showing a $^1$H-NMR spectrum and $^{13}$C-NMR spectrum of trimethylolpropane tris(2-mercaptoisobutyrate) (TPMIB).

(6) TPMIB $^1$H-NMR $^1$H-NMR of TPMIB was measured in deuterated chloroform by using the same apparatus as that for EGMB. The results obtained are shown in FIG. 11.

Figure 12:
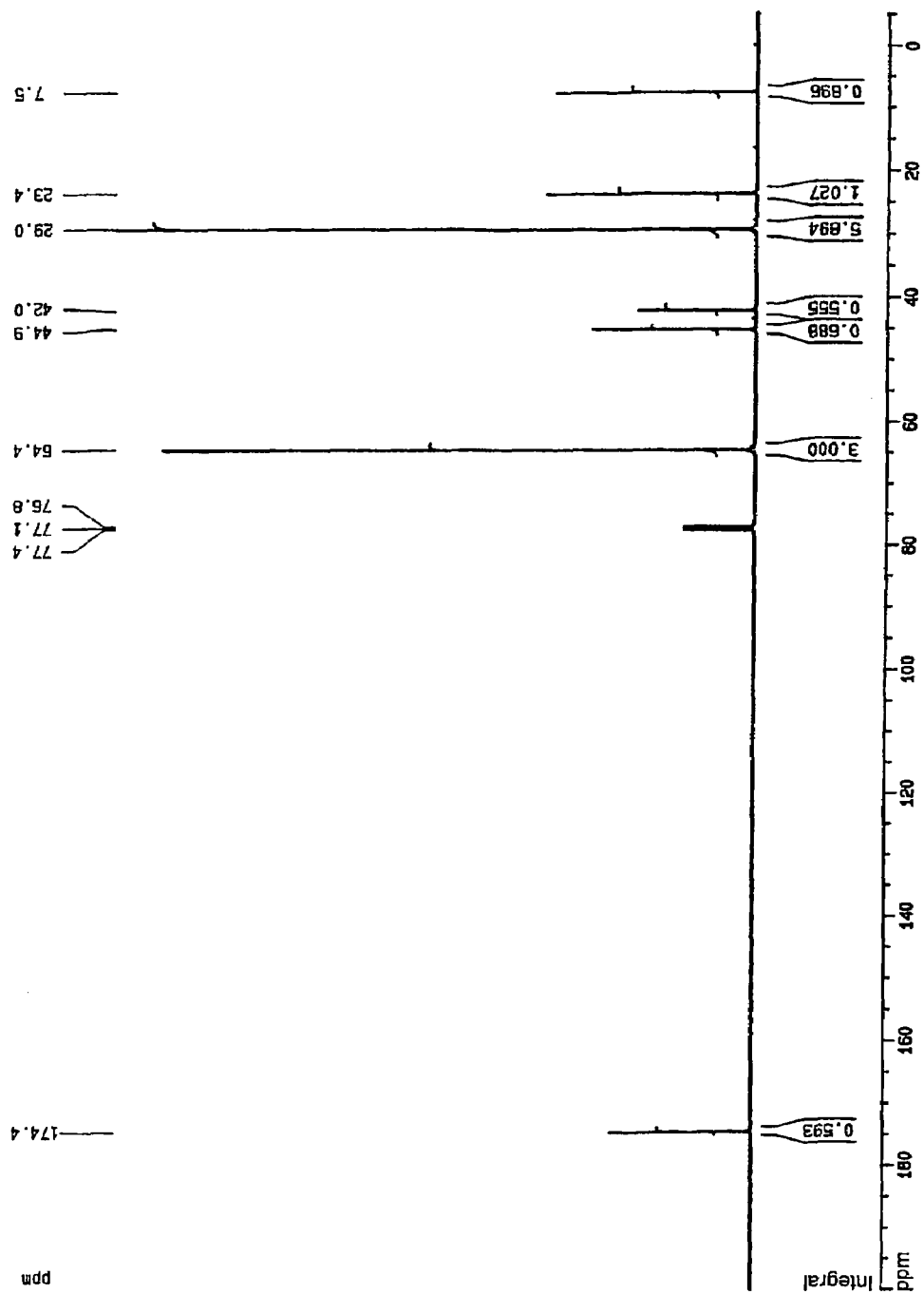

$^{13}$C-NMR $^{13}$C-NMR of TPMIB was measured in deuterated chloroform by using the same apparatus as that for EGMB and assignment of the peak of each chemical shift was performed. The results obtained are shown in FIG. 12.

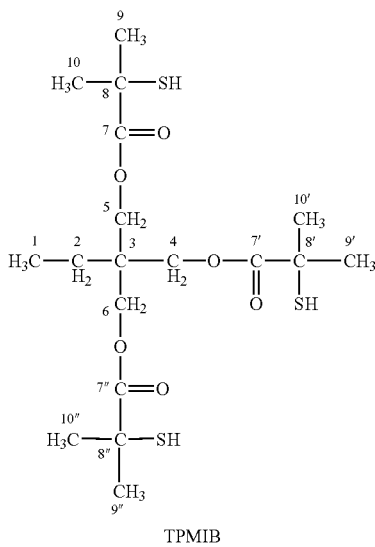

TPMIB

Trimethylolpropane tris(2-mercaptoisobutyrate)

| | |
|---|---|
| 7.5 ppm: | Carbon atom of 1-methyl group |
| 23.4 ppm: | Carbon atom of 2-methylene group |
| 29.0 ppm: | Carbon atoms of 9-, 9'-, 9''-, 10-, 10'-, and 10''-methyl groups |
| 42.0 ppm: | 3-quaternary carbon atom |
| 44.9 ppm: | 8-, 8'-, 8''-quaternary carbon atom |
| 64.4 ppm: | Carbon atoms of 4-, 5-, and 6-methylene groups |
| 174.7 ppm: | Carbon atoms of 7-, 7'-, and 7''-carbonyl groups |

Mass Spectrometry

For the mass spectrometry of TPMIB, measurements were performed by using the same apparatus as that for EGMB. The peak corresponding to $MH^+$ was detected at the position of m/z=441, which coincided with the molecular weight of TPMIB being 440.64.

Melting Point:

Melting point was measured by using a melting point measuring apparatus type 510, manufactured by BUCHI Co. The melting point measured was 60° C.

Production Example for Resin Solution:

In a 1-liter four-mouthed flask were charged 350 parts of cyclohexanone (manufactured by Wako Pure Chemical Industry Co., Ltd.), 26 parts of styrene (manufactured by Tokyo Kasei Kogyo Co., Ltd.), 23 parts of 2-hydroxyethyl acrylate (manufactured by Kyoeisha Chemical Co., Ltd.), 35 parts of methacrylic acid (manufactured by Kyoeisha Chemical Co., Ltd.), 21 parts of methyl methacrylate (manufactured by Kyoeisha Chemical Co., Ltd.), and 70 parts of n-butyl methacrylate (manufactured by Kyoeisha Chemical Co., Ltd.), and heated at 90° C. To this was added dropwise in 3 hours a previously prepared mixture in which 290 parts of cyclohexanone, 26 parts of styrene, 23 parts of 2-hydroxyethyl acrylate, 35 parts of methacrylic acid, 21 parts of methyl methacrylate, 70 parts of butyl methacrylate, and 1.75 parts of azobisisobutyronitrile (manufactured by Wako Pure Chemical Industry Co., Ltd.) were solved, and the mixture was further reacted at 90° C. for additional 3 hours. Further, a solution of 0.75 part of azobisisobutyronitrile in 10 parts of cyclohexanone was added thereto and the reaction was continued for additional 1 hour to synthesize a resin solution. A part of the resin solution was sampled, dried with heating at 180° C. for 20 minutes, and measured for nonvolatile portion, followed by adding cyclohexanone so that the previously synthesized resin solution contained 30% of the nonvolatile portion.

Preparation of Photosensitive Colored Composition

The photosensitive (colored) composition prepared in this example was called a resist for convenience's sake. Note that in this example, resist pattern formation with the alkali developable type resist in which a pigment was dispersed was performed by the following steps.

First step: the step of forming a photosensitive colored resin layer with the photosensitive composition of the present invention on a transparent substrate;

Second step: the step of performing pattern-wise exposure through a pattern mask having a predetermined pattern on the above-mentioned photosensitive colored resin layer;

Third step: the step of performing development treatment of the photosensitive colored resin layer after the above-mentioned pattern exposure to convert the photosensitive resin layer after the curing that remains on the above-mentioned transparent substrate in accordance with the predetermined pattern into a pixel layer; and Fourth step: the step of performing baking of the transparent substrate on which pixel layer is formed (post-baking).

In this example, since a super-high pressure mercury lamp was used as an exposure lamp, the sensitizer having an absorption wavelength region of 250 to 500 nm was used.

Examples 1 to 12

Fabrication of Blue Resist

A resin solution (50 parts), 5.7 part of Lionol Blue E (manufactured by Toyo Ink Manufacturing Co., Ltd.), and 0.3 part of a dispersant (BYK-161, manufactured by BYK Chemie Co.) were mixed and dispersed in a paint conditioner (manufactured Asada Iron Works Co., Ltd.) for 24 hours to prepare a blue dispersion.

Then, 50 parts of the blue dispersion, 6.25 parts of trimethylolpropane triacrylate (manufactured by Shinnakamura Chemical Industry Co., Ltd.; trade name NK Ester ATMPT), and 30.75 parts of cyclohexanone were sufficiently mixed in a vessel to prepare a blue resist having about 29% of nonvolatile components (without initiator).

In a vessel, 100 parts of the blue resist was sufficiently mixed with the sensitizer, photopolymerization initiator, and the thiol compound shown in Table 1, and the mixture was filtered through a 1.0-μm filter to prepare a blue resist having a nonvolatile components content of about 30%.

Measurement of sensitivity (described hereinbelow) was performed on the day when the resist was prepared and after storage at room temperature (22 to 24° C.) for four weeks.

Comparative Examples 1 and 2

In a vessel, 100 parts of the above-mentioned blue resist (without initiator) was mixed with the sensitizer and the photopolymerization initiator in Table 1, and the mixture was filtered through a 1.0-μm filter to prepare a blue resist having a nonvolatile components content of about 30%.

Comparative Examples 3 and 4

In a vessel, 100 parts of the above-mentioned blue resist (without initiator) was mixed with the sensitizer, the photopolymerization initiator, and the thiol compound in Table 1, and the mixture was filtered through a 1.0-μm filter to prepare a blue resist having a nonvolatile components content of about 30%. Note that as the thiol compound, trimethylolpropane tris(3-mercaptopropionate) (TPMP) (manufactured by Yodo Chemical Co., Ltd., trade name: TMTP) was used.

TABLE 1

| No. | Sensitizer (0.2 Part) | Photopolymerization initiator (0.8 Part) | Thiol Compound |
|---|---|---|---|
| Example | | | |
| 1 | None | 2-Hydroxy-2-methyl-1-phenylpropan-1-one | TPMB |
| 2 | None | 1-Hydroxycyclohexyl phenyl ketone | TPMB |
| 3 | None | 2-Methyl-1-[4-(methylthio)phenyl]-2-morpholino-propane-1-one | TPMB |
| 4 | Isopropyl thioxanthone | 2-Methyl-1-[4-(methylthio)phenyl]-2-morpholino-propan-1-one | TPMB |
| 5 | None | 2-Benzyl-2-dimethylamino-1-(morpholinophenyl)butan-1-one | TPMB |
| 6 | None | 2,2'-Bis(2-chlorophenyl)-4,4',5,5'-tetraphenylbiimidazole | TPMB |
| 7 | 4,4'-Bis(diethylamino)benzophenone | 2,2'-Bis(2-chlorophenyl)-4,4',5,5'-tetraphenylbiimidazole | TPMB |
| 8 | 4,4'-Bis(diethylamino)benzophenone | 2,2'-Bis(2-chlorophenyl)-4,4',5,5'-tetraphenylbiimidazole | TPMIB |
| 9 | 4,4'-Bis(diethylamino)benzophenone | 2,2'-Bis(2-chlorophenyl)-4,4',5,5'-tetraphenylbiimidazole | EGMB |
| 10 | 4,4'-Bis(diethylamino)benzophenone | 2,2'-Bis(2-chlorophenyl)-4,4',5,5'-tetraphenylbiimidazole | EGMIB |
| 11 | 4,4'-Bis(diethylamino)benzophenone | 2,2'-Bis(2-chlorophenyl)-4,4',5,5'-tetraphenylbiimidazole | PGMB |
| 12 | 4,4'-Bis(diethylamino)benzophenone | 2,2'-Bis(2-chlorophenyl)-4,4',5,5'-tetraphenylbiimidazole | PGMIB |
| Comparative Example | | | |
| 1 | Isopropyl thioxanthone | 2-Methyl-1-[4-(methylthio)phenyl]-2-morpholino-propan-1-one | None |
| 2 | 4,4'-Bis(diethylamino)benzophenone | 2,2'-Bis(2-chlorophenyl)-4,4',5,5'-tetraphenylbiimidazole | None |
| 3 | Isopropyl thioxanthone | 2-Methyl-1-[4-(methylthio)phenyl]-2-morpholino-propan-1-one | TPMP |
| 4 | 4,4'-Bis(diethylamino)benzophenone | 2,2'-Bis(2-chlorophenyl)-4,4',5,5'-tetraphenylbiimidazole | TPMP |

Isopropylthioxanthone: Manufactured by Lambson Fine Chemicals Ltd., SPEEDCURE ITX
4,4'-Bis(diethylamino)benzophenone: Produced by Hodogaya Chemical Co., Ltd., EAB-F
2-Hydroxy-2-methyl-1-phenylpropan-1-one: Produced by Ciba Specialty Chemicals Inc., Darocur 1173
1-Hydroxycyclohexyl phenyl ketone: Produced by Ciba Specialty Chemicals Inc., Irgacure 184
2-Methyl-1-[4-(methylthio)phenyl]-2-morpholino-propan-1-one: Produced by Ciba Specialty Chemicals Inc., Irgacure 907
2-Benzyl-2-dimethylamino-1-(morpholino)-butan-1-one: Produced by Ciba Specialty Chemicals Inc., Irgacure 369
2,2'-Bis(2-chlorophenyl)-4,4',5,5'-tetraphenylbiimidazole: Produced by Hodogaya Chemical Co., Ltd., B-CIM

Spectrophotometric Measurement of Resist

To measure spectrophotometric sensitivity of the obtained resist, each of the resists Examples and Comparative Examples was coated on a 100 mm×100 mm glass substrate to a dry film thickness of about 10 μm by using a spin coater and dried in a hot-air oven at 70° C. for 20 minutes. This was set in a irradiation spectrophotometer (manufactured by JASCO Corporation, CT-25CP type) and exposed with automatically varying the exposure time. As a light source, a super-high pressure mercury lamp was used. The substrate after the exposure was developed with an aqueous 0.5% sodium carbonate solution for about 40 seconds and subsequently rinsed with running water and heated at 220° C. for 30 minutes to obtain spectrograms. Table 2 shows number of remaining development steps with i-line (365 nm), h-line (405 nm), and g-line (436 nm). The relationship between the number of steps and exposure amount in the present experimental apparatus is as shown in Table 2. That is, the larger the number of steps, the higher the sensitivity.

TABLE 2

| Number of Steps | Exposure Amount (mJ/cm$^2$) |
|---|---|
| 13 | 1.00 |
| 12 | 1.78 |
| 11 | 3.16 |
| 10 | 5.62 |

TABLE 2-continued

| Number of Steps | Exposure Amount (mJ/cm²) |
|---|---|
| 9 | 10.0 |
| 8 | 17.8 |
| 7 | 31.6 |
| 6 | 56.2 |
| 5 | 100 |
| 4 | 177 |
| 3 | 316 |
| 2 | 562 |
| 1 | 1,000 |

The results obtained are shown in Table 3. As will be apparent from the results in Table 3, the photosensitive composition of the present invention has high sensitivity and excellent storage stability without forming an oxygen-shielding membrane and hence the present invention can provide a photosensitive composition that can reduce the number of production steps and makes it possible to reduce costs as a result of improvement of productivity.

TABLE 3

|  | Day 0 | | | Day 28 | | |
|---|---|---|---|---|---|---|
|  | i-line | h-line | g-line | i-line | h-line | g-line |
| Example 1 | 4 | 0 | 0 | 4 | 0 | 0 |
| Example 2 | 4 | 0 | 0 | 4 | 0 | 0 |
| Example 3 | 6 | 0 | 0 | 6 | 0 | 0 |
| Example 4 | 7 | 3 | 0 | 7 | 3 | 0 |
| Example 5 | 7 | 4 | 1 | 7 | 4 | 1 |
| Example 6 | 5 | 0 | 0 | 5 | 0 | 0 |
| Example 7 | 8 | 4 | 0 | 8 | 4 | 0 |
| Example 8 | 7 | 3 | 0 | 7 | 3 | 0 |
| Example 9 | 8 | 4 | 0 | 8 | 4 | 0 |
| Example 10 | 7 | 3 | 0 | 7 | 3 | 0 |
| Example 11 | 8 | 4 | 0 | 8 | 4 | 0 |
| Example 12 | 7 | 3 | 0 | 7 | 3 | 0 |
| Comparative Example 1 | 1 | 0 | 0 | 0 | 0 | 0 |
| Comparative Example 2 | 1 | 0 | 0 | 0 | 0 | 0 |
| Comparative Example 3 | 8 | 4 | 0 | 4 | 1 | 0 |
| Comparative Example 4 | 9 | 5 | 0 | 4 | 1 | 0 |

INDUSTRIAL APPLICABILITY

Use of the photopolymerization initiator composition containing the thiol compound of the present invention can give rise to a photosensitive composition having high sensitivity and excellent storage stability thereby enabling reduction in costs as a result of improvement of productivity.

The photosensitive composition of the present invention is used advantageously in application fields such as resists for printing plates, color proofs, solder resists, etching resists, color filter resists, holograms, optical imaging, and UV ink. In particular, it is suitable as a development type resist for forming precise patterns.

The inventoin claimed is:

1. A photopolymerization initiator composition, comprising a thiol compound having a mercapto group-containing group that has at least one substituent on carbon atom(s) at the α- and/or β-position to the mercapto group and a photopolymerization initiator, wherein at least one of the substituents on carbon atom(s) at the α- and/or β-position to the mercapto group is an alkyl group, wherein the thiol compound is a compound comprising a mercapto group-containing group represented by formula (1)

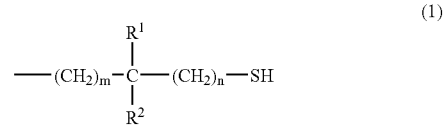

(1)

wherein $R^1$ and $R^2$ represent each independently a hydrogen atom or an alkyl group having 1 to 10 carbon atoms, provided that at least one of $R^1$ and $R^2$ is an alkyl group, and (m, n) is (1, 0), (1, 1), (2, 0) or (2, 1).

2. The photopolymerization initiator composition as claimed in claim 1, wherein the alkyl group is a straight chain or branched chain alkyl group having 1 to 10 carbon atoms.

3. The photopolymerization initiator composition as claimed in claim 1, wherein the thiol compound is a compound having two or more mercapto group-containing groups.

4. The photopolymerization initiator composition as claimed in claim 1, wherein the thiol compound having a mercapto group-containing group is an ester compound derived from a mercapto group-containing carboxylic acid represented by formula (2) and a polyfunctional alcohol

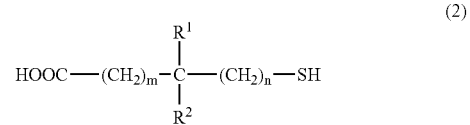

(2)

wherein the symbols have the same meaning as defined in claim 1.

5. The photopolymerization initiator composition as claimed in claim 4, wherein the polyfunctional alcohol is one or more compounds selected from a group consisting of an alkylene glycol (provided that the alkylene group has 2 to 10 carbon atoms and may be branched), diethylene glycol, dipropylene glycol, glycerol, trimethylolpropane, pentaerythritol, and dipentaerythritol.

6. The photopolymerization initiator composition as claimed in claim 5, wherein the alkylene glycol is ethylene glycol, 1,2-propylene glycol or 1,2-butanediol.

7. The photopolymerization initiator composition as claimed in claim 4, wherein the thiol compound is a compound represented by formula (A)

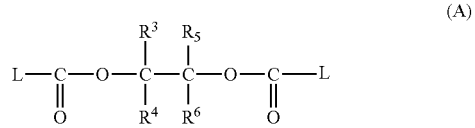

(A)

wherein $R^3$ to $R^6$ represent each independently a hydrogen atom or an alkyl group having 1 to 10 carbon atoms, and L is a group represented by formula (1)

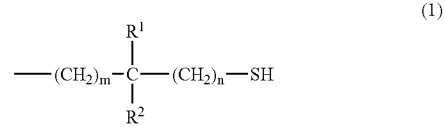

(1)

wherein $R^1$, $R^2$, m and n have the same meanings as defined in claim 1.

8. The photopolymerization initiator composition as claimed in claim 4, wherein the thiol compound is a compound represented by formula (B)

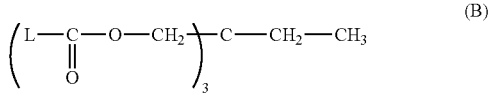

wherein L is a group represented by formula (1)

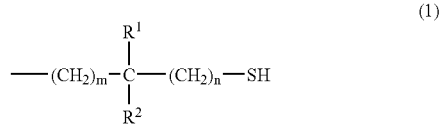

wherein $R^1$, $R^2$, m and n have the same meanings as defined in claim 1.

9. The photopolymerization initiator composition as claimed in claim 4, wherein the thiol compound having a mercapto group-containing group is a compound selected from ethylene glycol bis(3-mercaptobutyrate), 1,2-propylene glycol (3-mercaptobutyrate), and trimethylolpropane tris(3-mercaptobutyrate).

10. The photopolymerization initiator composition as claimed in claim 1, wherein n is 0.

11. The photopolymerization initiator composition as claimed in claim 1, wherein the photopolymerization initiator is at least one photopolymerization initiator selected from a group consisting of α-hydroxyacetophenones, α-aminoacetophenones, and biimidazoles.

12. The photopolymerization initiator composition as claimed in claim 1, wherein the composition further comprises a sensitizer.

13. The photopolymerization initiator composition as claimed in claim 12, wherein the sensitizer is selected from a group consisting of benzophenones and anthraquinones.

14. A photosensitive composition containing the photopolymerization initiator composition as claimed in claim 1.

15. The photosensitive composition as claimed in claim 14, wherein the composition contains a polymer compound and/or a compound having an ethylenically unsaturated bond.

16. The photosensitive composition as claimed in claim 15, wherein the polymer compound is soluble in a solvent or an aqueous alkali solution.

17. The photosensitive composition as claimed in claim 14, wherein the composition contains a pigment.

18. A thiol compound which is an ester compound derived from a mercapto group-containing carboxylic acid represented by formula (2) and a polyfunctional alcohol

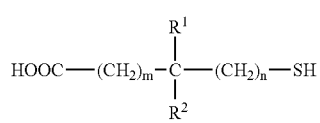

wherein $R^1$ and $R^2$ represent each independently a hydrogen atom or an alkyl group having 1 to 10 carbon atoms, provided that at least one of $R^1$ and $R^2$ is an alkyl group, and (m, n) is (1, 1), (2, 0) or (2, 1).

19. The thiol compound as claimed in claim 18, wherein the polyfunctional alcohol is one or more compounds selected from a group consisting of an alkylene glycol (provided that the alkylene group has 2 to 10 carbon atoms and may be branched), diethylene glycol, dipropylene glycol, glycerol, trimethylolpropane, pentaerythritol, and dipentaerythritol.

20. The thiol compound as claimed in claim 19, wherein the alkylene glycol is ethylene glycol, 1,2-propylene glycol or 1,2-butanediol.

21. The thiol compound as claimed in claim 18, wherein the thiol compound is represented by formula (A)

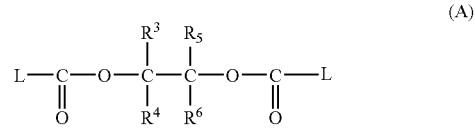

wherein $R^3$ to $R^6$ represent each independently a hydrogen atom or an alkyl group having 1 to 10 carbon atoms, and L is a group represented by formula (1)

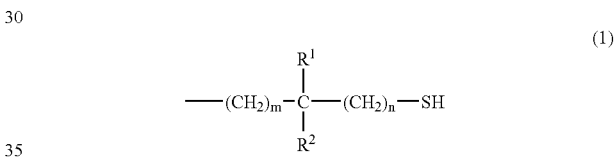

wherein $R^1$, $R^2$, m and n have the same meanings as defined in claim 18.

22. The thiol compound as claimed in claim 18, wherein the thiol compound is represented by formula (B)

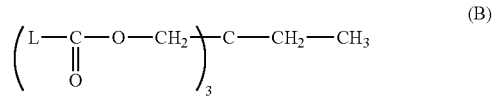

wherein L is a group represented by formula (1)

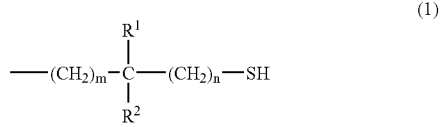

wherein $R^1$, $R^2$, m and n have the same meanings as defined in claim 18.

23. The thiol compound as claimed in claim 18, 21 or 22, wherein n is 0.

24. The thiol compound as claimed in claim 18, wherein the thiol compound has a molecular weight of 200 to 1,000.

* * * * *